US009889232B2

(12) United States Patent
Schubert

(10) Patent No.: US 9,889,232 B2
(45) Date of Patent: Feb. 13, 2018

(54) IMPLANTABLE LIPOSOME EMBEDDED MATRIX COMPOSITION, USES THEREOF, AND POLYCAPROLACTONE PARTICLES AS SCAFFOLDS FOR TISSUE REGENERATION

(71) Applicant: Shai Yehoshua Schubert, Brookline, MA (US)

(72) Inventor: Shai Yehoshua Schubert, Brookline, MA (US)

(73) Assignee: BONUS CELLORA LTD., Haifa (IL)

( * ) Notice: Subject to any disclaimer, the term of this patent is extended or adjusted under 35 U.S.C. 154(b) by 0 days.

(21) Appl. No.: 14/531,340

(22) Filed: Nov. 3, 2014

(65) Prior Publication Data

US 2015/0050332 A1 Feb. 19, 2015

Related U.S. Application Data

(62) Division of application No. 13/130,969, filed as application No. PCT/US2009/065797 on Nov. 24, 2009, now abandoned.

(60) Provisional application No. 61/200,208, filed on Nov. 24, 2008, provisional application No. 61/200,213, filed on Nov. 24, 2008, provisional application No. 61/200,207, filed on Nov. 24, 2008, provisional application No. 61/200,214, filed on Nov. 24, 2008.

(51) Int. Cl.

| | |
|---|---|
| A61K 9/00 | (2006.01) |
| A61K 31/00 | (2006.01) |
| A61K 38/00 | (2006.01) |
| A61K 47/48 | (2006.01) |
| A61L 27/54 | (2006.01) |
| A61K 48/00 | (2006.01) |
| A61L 27/18 | (2006.01) |
| A61L 27/38 | (2006.01) |
| A61L 27/48 | (2006.01) |
| A61L 27/22 | (2006.01) |
| A61L 27/24 | (2006.01) |
| A61L 27/44 | (2006.01) |
| A61L 27/52 | (2006.01) |

(52) U.S. Cl.
CPC .......... *A61L 27/54* (2013.01); *A61K 48/0016* (2013.01); *A61L 27/18* (2013.01); *A61L 27/222* (2013.01); *A61L 27/24* (2013.01); *A61L 27/3804* (2013.01); *A61L 27/44* (2013.01); *A61L 27/48* (2013.01); *A61L 27/52* (2013.01); *A61L 2300/232* (2013.01); *A61L 2300/252* (2013.01); *A61L 2300/258* (2013.01); *A61L 2300/426* (2013.01); *A61L 2300/438* (2013.01); *A61L 2300/45* (2013.01); *A61L 2300/626* (2013.01); *A61L 2400/06* (2013.01)

(58) Field of Classification Search
None
See application file for complete search history.

(56) References Cited

U.S. PATENT DOCUMENTS

| | | | |
|---|---|---|---|
| 5,879,713 A * | 3/1999 | Roth et al. | 424/489 |
| 6,132,765 A | 10/2000 | DiCosmo et al. | |
| 6,398,816 B1 | 6/2002 | Breitbart et al. | |
| 6,475,516 B2 | 11/2002 | DiCosmo et al. | |
| 7,427,602 B1 | 9/2008 | Shea et al. | |
| 2002/0034501 A1* | 3/2002 | Pawliuk et al. | 424/93.21 |
| 2002/0051812 A1 | 5/2002 | DiCosmo et al. | |
| 2003/0148979 A1* | 8/2003 | Sosnowski et al. | 514/44 |
| 2004/0132679 A1* | 7/2004 | Chan et al. | 514/44 |
| 2004/0265391 A1* | 12/2004 | Danenberg et al. | 424/490 |
| 2005/0069518 A1 | 3/2005 | Mousa et al. | |
| 2005/0186240 A1 | 8/2005 | Ringeisen et al. | |
| 2006/0140914 A1* | 6/2006 | Jain et al. | 424/93.7 |
| 2006/0228417 A1 | 10/2006 | Hubert et al. | |
| 2007/0148220 A1 | 6/2007 | Muller et al. | |

(Continued)

FOREIGN PATENT DOCUMENTS

| | | |
|---|---|---|
| WO | WO-9640062 A1 | 12/1996 |
| WO | WO-0154735 A2 | 8/2001 |
| WO | WO-05082431 A1 | 9/2005 |

OTHER PUBLICATIONS

Ruhnke et al. Differentiation of In Vitro-Modified Human Peripheral Blood Monocytes Into Hepatic-like and Pancreatic Islet-like Cells. Gastroenterology, 2005. 128:1774-1786.*
Kuenzler, JF. 2002. "Hydrogels." in: Encyclopedia of Polymer Science and Technology (Mark, HF, ed.) pp. 691-722.*
Pinhal-Enfield. An Angiogenic Switch in Macrophages Involving Synergy between Toll-Like Receptors 2,4,7 and 9 and Adenosine A2A Receptors. American Journal of Pathology, 2003. 163(2): 711-721.*

(Continued)

*Primary Examiner* — Maria Leavitt
*Assistant Examiner* — Kimberly A Aron
(74) *Attorney, Agent, or Firm* — The Roy Gross Law Firm, LLC; Roy Gross

(57) ABSTRACT

In various embodiments, the present invention describes materials and methods for the local reprogramming of cells in a location where the treatment is applied. The invention can be used to replace lost cells or to restore function to tissue damaged due to disease, injury or genetic defect. In various embodiments, the treatment includes a semisolid hydrogel embedded with liposomes. The liposomes can contain an effector molecule or molecules. When phagocytic cells such as monocytes infiltrate the hydrogel, they encounter the liposomes and incorporate the liposomes carrying the effector molecules into the cells. In some embodiments, the effector molecules can induce angiogenesis. The matrix can contain other effector molecules designed to attract specific cells to the matrix. The cells can also remain in the matrix and secret molecules such as proteins and hormones that will diffuse through the matrix material to the surrounding tissue.

24 Claims, No Drawings

(56) References Cited

U.S. PATENT DOCUMENTS

| | | |
|---|---|---|
| 2007/0224280 A1 | 9/2007 | Lillard et al. |
| 2009/0104254 A1* | 4/2009 | Sinko et al. .......... 424/450 |
| 2011/0287086 A1 | 11/2011 | Grayburn et al. |

OTHER PUBLICATIONS

Guo T, et al., Porous chitosan-gelatin scaffold containing plasmid DNA encoding transforming growth factor-beta1 for chondrocytes proliferation. Biomaterials. Mar. 2006;27(7):1095-103.

Ho E, et al., Synthesis and characterization of an injectable hydrogel with tunable mechanical properties for soft tissue repair. Biomacromolecules. Nov. 2006;7(11):3223-8.

Hou, Q, et al., Injectable scaffolds for tissue regeneration. J. Mater.Chem., vol. 14:1915-1923 (2004).

International Preliminary Report on Patentability and Written Opinion for Application No. PCT/US2009/065797, 7 pages, dated May 24, 2011.

International Search Report for Application No. PCT/US2009/065797, 3 pages, dated Aug. 30, 2010.

Kobsa S, et al., Bioengineering approaches to controlled protein delivery. Pediatr Res. May 2008;63(5):513-9.

Ruel-Gariépy E, et al., Thermosensitive chitosan-based hydrogel containing liposomes for the delivery of hydrophilic molecules. J Control Release. Aug. 21, 2002;82(2-3):373-83.

Supplementary European Search Report and Written Opinion for Application No. 09828393.0, 9 pages, dated Mar. 12, 2013.

Werning, M., et al., Neurons derived from reprogrammed fibroblasts functionally integrate into the fetal brain and improve symptoms of rats with Parkinson's disease, PNAS, vol. 105(15):5856-5861 (2008).

Yamanaka S. Induction of pluripotent stem cells from mouse fibroblasts by four transcription factors. Cell Prolif. Feb. 2008;41 Suppl 1:51-6.

Zhou Q, et al., In vivo reprogramming of adult pancreatic exocrine cells to beta-cells. Nature. Oct. 2, 2008;455(7213):627-32.

Clark et al., "$A_1$ Adenosine Receptor Activation Promotes Angiogenesis and Release of VEGF From Monocytes", Circulation Research, vol. 101, pp. 1130-1138 (2007).

Feoktistov et al., "Mast Cell-Mediated Stimulation of Angiogenesis: Cooperative Interaction Between A2B and A3 Adenosine Receptors", Circulation Research, vol. 92, pp. 485-492 (2003).

Grant et al., "Adenosine Receptor Activation Induces Vascular Endothelial Growth Factor in Human Retinal Endothelial Cells", Circulation Research, vol. 85, pp. 699-706 (1999).

Gu et al., "Adenosine upregulates VEGF expression cultured myocardial vascular smooth muscle cells", American Physiological Society, pp. H595-H602 (1999).

Hasko et al., "Shaping of monocyte and macrophage function by adenosine receptors", Pharmacology & Therapeutics, vol. 113, pp. 264-275 (2007).

Leibovich et al., "Synergistic Up-Regulation of Vascular Endothelial Growth Factor Expression in Murine Macrophages by Adenosine $A_{2A}$ Receptor Agonists and Endotoxin", American Journal of Pathology, vol. 160, No. 6, pp. 2231-2244 (2002).

Lienau et al., "Differential Regulation of Blood Vessel Formulation between Standard and Delayed Bone Healing", Journal of Orthopaedic Research, pp. 1133-1140 (2009).

Takagi et al., "Adenosine Mediates Hypoxic Induction of Vascular Endothelial Growth Factor in Retinal Pericytes and Endothelial Cells", Investigative Ophthalmology & Visual Science, vol. 37, No. 11, pp. 2165-2176 (1996).

* cited by examiner

IMPLANTABLE LIPOSOME EMBEDDED MATRIX COMPOSITION, USES THEREOF, AND POLYCAPROLACTONE PARTICLES AS SCAFFOLDS FOR TISSUE REGENERATION

RELATED APPLICATIONS

This application claims the benefit of priority from U.S. Ser. No. 61/200,208, filed Nov. 24, 2008; U.S. Ser. No. 61/200,213, filed Nov. 24, 2008; U.S. Ser. No. 61/200,207, filed Nov. 24, 2008; and 61/200,214, filed Nov. 24, 2008. The contents of the foregoing applications are incorporated herein by reference in their entirety.

BACKGROUND OF THE INVENTION

Delivery of bioactive molecules or chemical compounds to specific sites in vivo can be effected by embedding the molecules or compounds in a matrix. However, a common problem of matrix based delivery systems is the diffusion of compounds embedded in the matrix into the surrounding tissue, changing the concentration of the compound in the matrix and affecting its bioactivity.

SUMMARY OF THE INVENTION

The present invention is based on the development of compositions and methods for delivery of compounds encapsulated in liposomes. Embodiments of the invention feature liquid, semi-solid and solid matrices containing embedded liposomes, and methods for their formation and use. Through phagocytosis, monocytes infiltrating the matrix selectively incorporate the liposomes and their contents. The matrices may be injectable or implantable.

In exemplary embodiments, liposomes are introduced to a matrix (hydrogel) and are embedded in the matrix. The matrix can include one or more agents for recruiting cells (e.g., monocytes) to the matrix. Liposomes may encapsulate agents before being contacted with a matrix of the invention in some embodiments. In some embodiments, a matrix of the invention is formulated to incorporate agents and compounds that exert one or more effects upon cells which infiltrate the matrix. In other embodiments, a matrix of the invention is formulated to incorporate agents and compounds that attract cells (e.g., monocytes) to the matrix. In additional embodiments, the matrix is permeable for cells to enter or exit the matrix and to compounds produced by infiltrating cells. Compounds produced or secreted by cells within a matrix may diffuse out of the matrix and create effects in the surrounding environment in some embodiments. Additional embodiments of the invention include kits comprising a matrix of the invention and instructions for practicing the invention. In some embodiments, a kit of the invention includes matrix and one or more reagents for preparing liposomes for incorporation therein.

In other embodiments, the invention relates to methods of using polycaprolactone (PCL) particles as biodegradable scaffolds in tissue engineering applications.

DETAILED DESCRIPTION OF THE INVENTION

I. Definitions

In order that the present invention may be more readily understood, certain terms are first defined.

Monocytes are mononuclear phagocytic leukocytes formed in the bone marrow that transport to tissues where they develop into a wide variety of cells, including macrophages. The term "monocytic cell" as used herein refers both to monocytes and any cell terminally differentiated from monocytes (e.g., macrophages), as well as cells capable of differentiating into monocytes. Thus, the term "monocytic cell" includes not only differentiated monocytes, but also pluripotent stem cell and committed progenitor cells which differentiate into monocytes, as well as other effector cells which terminally differentiate from monocytes (e.g., macrophages and/or mononuclear phagocytes, and the like). These other cells are well-known and have been previously described (Zhao, et al., Proc Natl Acad Sci USA, 2003, 100:2426-31, Strauss-Ayali, et al., J Leukoc Biol, 2007, 82:244-52, Tacke and Randolph, Immunobiology, 2006, 211:609-18, Vega, M A et al, Inmunologia 2006, 25(4): 248-272). The term "monocytic cell" also includes monocyte-derived multipotential cells (MOMC), which can display morphological and phenotypic features of endothelial and mesenchymal cells (Seta and Kuwana, Keio J Med, 2007, 56:41-47).

The term "polymer" as used herein refers to any monomer or polymer molecular species that can be polymerized to form a matrix of the invention. As such, a solution containing one or more polymers may contain a chemical species comprising one subunit of a polymer compound (e.g., a monomer) or two or more subunits covalently linked with each other. In some embodiments, a polymer for use in creating matrix of the invention will have one or more reactive groups per molecule. In some embodiments, a polymer may have an essentially linear structure. In some embodiments, a polymer may have a branched structure, comprising at least one branch point from which two or more portions of the polymer molecule originate.

The term "linker" as used herein refers to connections between molecules of the polymer network wherein one or molecules is bound or physically associated with two or more other molecules of the polymer network simultaneously.

The term "matrix" as used herein refers to a liquid, semi-solid or solid polymer substance (e.g., cross-linked polymeric substance) that has the capacity to comprise cells. In preferred embodiments, the term "matrix" refers to a biodegradable hydrogel that may be in any polymerization state.

The term "hydrogel" as used herein refers to a polymeric substance that absorbs at least 90% of its weight in water.

The term "semisolid matrix" as used herein refers to a composition of matter that has a rigidity and viscosity intermediate between a solid and a liquid e.g., a gel.

Biocompatible materials are generally considered to be materials that perform with an appropriate host response in a specific application, with the additional quality of not having toxic or injurious effects on biological systems. The term "biocompatible" as used herein refers to the ability of a hydrogel to perform with an appropriate host response when delivered as described in the present invention.

The term "liposome" as used herein refers to microscopic vesicles comprising an outer lipid layer. In some embodiments, the outer lipid layer is a lipid bilayer. In other embodiments, the outer lipid layer of the liposomes described herein is a lipid monolayer. In such embodiments where the outer lipid layer is a lipid monolayer, the liposomes are also referred to as micelles.

The term "liposome matrix" as used herein refers to a matrix into which liposomes are embedded.

The term "tumor antigen" as used herein refers to any antigenic material present in a tumor cell. A tumor antigen is preferably a polypeptide. In some embodiments, a tumor antigen is a polypeptide that is present on the outer surface of a tumor cell. In some embodiments, a tumor antigen is expressed at a higher level in a tumor cell than in a normal, non-tumorigenic cell. In other embodiments, a tumor antigen is expressed in a tumor cell and is not expressed in a normal cell. A tumor antigen, or a mixture of tumor antigens, may be obtained from a tumor cell or a tumor tissue, e.g., tissue from a tumor biopsy. A tumor antigen can also be produced recombinantly. In some embodiments, a tumor antigen is purified from a tumor cell or a tumor tissue extract. In other embodiments, a tumor antigen is used in the compositions and methods of the invention without purification. A tumor antigen may be obtained from a tumor in a subject, encapsulated in liposomes embedded within a liposome matrix, and implanted into the same subject, in accordance with the methods of the invention. A tumor antigen may also be obtained from other sources. Accordingly, a tumor antigen used in the compositions and methods described herein can be allogeneic or syngeneic with respect to a subject to whom the tumor antigens are administered as part of a liposome matrix.

II. Liposomes

Aspects of the invention include one or more liposomes carrying one or more compounds such as a small molecule, a protein, a polypeptide, DNA, RNA or other genetic material such as an siRNA, a small molecule, a drug or a chemical composition.

Liposomes are microscopic vesicles comprising an outer lipid layer. In some embodiments, the outer lipid layer is a lipid bilayer. In other embodiments, the outer lipid layer of the liposomes described herein is a lipid monolayer. In such embodiments where the outer lipid layer is a lipid monolayer, the liposomes are also referred to as micelles 1Reagents suitable for producing liposomes include, but are not limited to, a phospholipid such as distearoyl-phosphatidylglycerol (DSPG), 1,2-distearoyl-sn-glycero-3-phosphocholine (DSPC), dioleoyl phosphatidyl choline (DOPC), dioleoyl phosphatidylglycerol (DOPG), phosphatidylglycerol (PC), phosphatidic acid (PA), and/or phosphatidylglycerol (PG). The saturated lipids, including but not limited to Dimyristoylphosphatidylcholine (DMPC), dipalmitoyl phosphatidylcholine (DPPC), dipalmitoyl phosphatidic acid (DPPA), and dipalmitoyl phosphatidylglycerol (DMPG) can also be used in liposome production. In some embodiments, stearylamine can be used when cationic liposomes are preferred, and natural acidic lipids, such as phosphatidylserine (PS), PG, phosphatidylinositol (PI), PA, and cardiolipin (CL) can be added when anionic liposomes are desired. In some embodiments, cholesterol can be included to stabilize a liposome bilayer. Small amounts of antioxidants, including but not limited to α-tocopherol or β-hydroxytoluidine (BHT), can be included when polyunsaturated neutral lipids are used.

The core of the liposome is aqueous and can be used to hold different compounds such as small molecules, drugs, polypeptides, or genetic material (DNA, RNA, cDNA, siRNA). Hydrophilic compounds can be trapped inside the liposome, while hydrophobic compounds can be carried in the lipid portion of the liposome. Liposomes range in size from 20 nanometers to over 1000 nanometers. Accordingly, liposomes may be 20 nm, 25 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 950 nm, or 100 nm. In exemplary embodiments, the liposomes range from 100 nm to 200 nm. The size of the liposomes can be controlled by methods such as sonication and filtration. Liposomes are diverse and can be formed in different sizes and lipid compositions. Additional properties and methods of making liposomes are further described in Basu, Subhash C.; Basu, Manju (Eds.) Liposome Methods and Protocols, Methods in Molecular Biology, Vol. 199, (2002); and in Liposome Technology, Third Edition, by Gregory Gregoriadis (Editor), Informa HealthCare, (Sep. 12, 2006), the entire contents of which are incorporated herein by reference in their entirety.

Different types of liposomes include Sterically Protected Liposomes such as PEGylated liposome. Liposomes can optionally be surface modified liposomes, such as liposomes in which proteins have been incorporated at the surface for interaction with cells. Such proteins include, but are not limited to, antibodies, peptides, receptors, and other proteins having the capacity to interact with cell-surface receptors. Binding of proteins and peptides to liposomes may be accomplished through amino acid groups or through sulfhydryl groups. Carbohydrates and other small molecules may likewise be bound to the liposomal surface. Liposome modifications can be used in order to target specific cells by, for example, incorporating specific ligand that will bind to a specific cell receptor. Surface modification can also be used to attach the liposome to the matrix. Liposomes can optionally be produced to carry positive or negative charge. The charge of the liposome can be used in order to keep the liposome in the matrix. For example, positively charged liposomes will be attracted to a negatively charged matrix. The combination of liposome size versus matrix pore size and liposome electrical charge can be used to maintain the liposomes in the matrix.

III. Matrix Compositions

The present invention features liposomes embedded in certain matrices for delivery to target sites (e.g., at desired sites of injection, implantation, and the like). A matrix of the invention can include activating and/or polarizing agents as described herein for the purpose of activating, further activating, polarizing, further polarizing and/or maintaining the activation or polarization state of infiltrating monocytic cells.

Aspects of the invention include one or more hydrogels, which may comprise polylactic acid, polyglycolic acid, other polyhydroxy acids, copolymers of two or more polyhydroxy acids, polyorthoesters, polyanhydrides, polycaprolactone, gelatin, collagen, cellulose, derivatized cellulose, chitosan, alginate, thiol-modified hyaluronan, and/or combinations thereof. In some embodiments, a cross-linking agent is comprised by a kit of the invention and may comprise glutaraldehyde, diphenylphosphoryl azide, transglutaminase, dimethyl suberimidate, self assembling proteins or peptides, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, and tripolyphosphate.

The matrix used with embodiments of the invention can be a biocompatible matrix suitable for implanting in contact adjacent to, or at the site of, the target tissue or at a site where localized recruitment of phagocytic cells, e.g., monocytes is therapeutically desired. Preferably, the matrix is a biodegradable material, such as a synthetic polymer degrading by hydrolysis, for example, polyhydroxy acids like polylactic acid, polyglycolic acid and copolymers thereof, polyorthoesters, polyanhydrides, proteins such as gelatin and collagen, or carbohydrates or polysaccharides such as cellulose and derivatized celluloses, chitosan, alginate, thiol-modified hyaluronan or combinations thereof, so that over the course of several days or weeks after implantation of the matrix material, the matrix gradually disappears. In a preferred embodiment, the matrix is a hydrogel, defined as a matrix wherein typically approximately 90% by weight of the matrix is absorbed with water. Other hydrogels for use with embodiments of the invention can be formed by ionic or covalent cross linking of a variety of water soluble polymers such as polyphosphazenes, polysaccharides such as alginate, and proteins such as gelatin.

In certain embodiments, the hydrogel material will be capable of forming a semi-solid matrix on its own. One example of such a hydrogel material is liquid collagen in physiologic pH which converts to a semisolid state upon exposure to body temperature. In other embodiments, when the hydrogel material cannot on its own form a semisolid matrix or produce the desired physical properties, the matrix will further comprise a cross-linking agent which will form the semisolid matrix with the hydrogel material. Examples of cross-linking agents useful in the matrix of this invention include, but are not limited to, glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, and tripolyphosphate.

In certain embodiments, the matrix is biodegradable through hydrolysis of the hydrogel polymer. The stability of the matrix to degradation can be altered through the use of different hydrogel materials, different cross-linking agents and combinations thereof. The desired stability of the matrices of this invention ranges from several days to several weeks, depending upon the disease or condition to be treated by the matrix. In some embodiments, the hydrogel material and/or the matrix will initially be in a liquid state and then converted to a semisolid state through one or more of the following: change in pH, the addition of copolymer(s), irradiation, temperature change, the addition of a catalyzer, or the addition of a cross linker. Such liquid compositions are also part of the present invention.

In both a liquid state and in the final semi-solid state, the matrix of this invention is injectable into a patient at the site of desired treatment. Thus, according to one embodiment, the invention provides an injectable composition comprising:
a. a hydrogel; and
b. liposomes containing a desired product, wherein the composition is in or is convertible to a semisolid state.

Polymer consistency in the matrix can be manipulated to produce soft or hard matrices for different delivery methods such as injection or implantation.

According to some embodiments, the matrix may additionally comprise an insoluble, hydratable biocompatible polymer scaffold, such as Gelfoam®. In these embodiments, the liposomes are typically adhered to the scaffold and then the scaffold containing the adhered liposomes is surrounded by the semisolid hydrogel (and optionally a cross-linker).

A matrix of the invention may be formulated with a variety of different polymer ingredients and polymers in different states in order to achieve desired attributes in the matrix. For example, in some embodiments of the invention, solid collagen or gelatin particles or granules are mixed with liquid collagen before introduction of liposomes and delivery to an organism. This is done to create a matrix with a reduced tendency for dispersion than a matrix formed with liquid collagen alone. In some embodiments, a matrix can be formulated with a combination of polymers of different types and/or different physical states to create a matrix with particular dimensions or attributes upon delivery. Matrices of the invention may be formulated with a particular polymer or a particular combination of polymers (of different molecular formulas and/or physical states) to enhance cohesion of the matrix upon delivery and/or to reduce immersion of the matrix into tissues, fibers, internal spaces or other structures or voids within the organism. In some embodiments, use of a particular polymer or a particular combination of polymers used to formulate a matrix creates a matrix upon delivery that has a reduced surface area in relation to volume as compared to a matrix formulated with one kind of polymer alone. In certain embodiments, a matrix with a reduced surface area to volume ratio can have a more spherical shape.

The semisolid hydrogel matrix can be injected via a syringe or implanted during a surgical procedure. Depending on the specific indication, the matrix is designed to degrade in 1 to 180 days. Depending on the specific indication, the matrix may contain chemoattractants to attract specific cell types.

IV. Modulation of Monocyte Behavior Using Liposome Embedded Matrix

Monocytes are a type of leukocyte, or white blood cell, which have an integral role in the innate immune system. Following the appearance of signals delivered from a specific site in the body, monocytes are mobilized by chemotactic signals and adhere to the activated endothelium through interactions mediated by adhesion molecules including P-CAM, V-CAM and I-CAM on endothelial cells and CD18 and CD11B on monocytes. Following their adhesion to the endothelium, monocytes transmigrate into the tissue and differentiate into macrophages.

Together with neutrophils, eosinophils and natural killer cells, monocytes function as a first-line defense to detect, eliminate or contain invading microbes and toxic macromolecules. Monocytes responses towards these targets are rapid and triggered by structures, commonly referred to as Pathogen-Associated Molecular Patterns (PAMP). Whenever the innate immunity is unable to handle an invading microorganism, monocytes function as effector cells of the adaptive immune system, after receiving the appropriate activation and information from antigen-specific T and B-lymphocytes.

Monocytes have also essential functions in wound healing and resolution of inflammation, mediating cell migration, extra-cellular matrix remodeling and angiogenesis, all of which are required for tissue repair.

Consequently, an ultimate goal of monocytes is the maintenance of tissue homeostasis and integrity. This is achieved by various monocyte functions, such as, secretion of specific proteins, scavenging, elimination of pathogen and tumor cells, clearance of senescent cells, control of tissue cell growth and modulation of the extra-cellular milieu.

To accomplish these tasks, monocytes exhibit a highly flexible gene expression program that allows them to adapt and respond to changes in their surrounding micro-environment, as well as to recruit, engage and coordinate other cell types in restoring normal tissue structure and function.

These various monocyte activities are not displayed concomitantly and, in fact, some of these activities are clearly contradictory (e.g., degradation versus synthesis of extracellular matrix). Thus, tissue monocytes are functionally heterogeneous under basal conditions, and exhibit a large degree of variability upon activation by endogenous factors or exogenous stimuli (see Vega, M A et al, Immunologia 2006, 25(4): 248-272).

Monocyte implantation at site of ischemic tissue has been attempted as a therapeutic approach for the treatment of various conditions such as cancer, heart disease, ischemia, nerve injury, wound healing and diabetes. Similarly, monocyte therapy has been used for the delivery of therapeutic proteins by genetic manipulation, activation or transformation of the monocytes (Muhlebach, M. D., et al., Mol Ther, 2005. 12:1206-16; Lu, Y., et al., Cell Mol Biol, 2003. 49:1151-6; Spiekermann, K., et al., Eur J Haematol, 2001. 67:63-71; US 2006/0257359). The use of monocytes has also been described for nerve repair and spinal cord injury treatment (Lazarov-Spiegler, O., Solomon, A. S., and Schwartz, M. Glia, 1998. 24:329-37; Rapalino, O., et al., Nat Med, 1998. 4:814-21; Schwartz, M., et al., Neurosurgery, 1999. 44:1041-6; U.S. Pat. No. 6,267,955).

While some progress has been made in the field of cellular therapy and therapeutic protein delivery for tissue repair, there exists a need to improve the ability to manipulate monocyte behavior in vivo.

Monocytes have the potential to differentiate and adopt different cell phenotypes based on their microenvironment and the molecules to which they are exposed (Mantovani, A. et al, Trends Immunol 2004, 25: 677-686; Mantovani, A et al, Immunity 2005, 23:344-346; Mantovani, A et al, Eur J Immunol 2007, 37:14-16; Pinhal-Enfield, G et al, Am J Pathol 2003, 163:711-721; Zhao, Y et al., Proc Natl Acad Sci USA 2003, 100:2426-2431; Mantovani, A, Blood 2006, 108(2):408-409). In the body, monocytes routinely migrate from the blood circulation into different tissues and organs where they differentiate into resident macrophages and spend the majority of their life span.

In various embodiments, the present invention is based on the development of compositions and methods for delivery of compounds encapsulated in liposomes. Embodiments of the invention feature liquid, semi-solid and solid matrices containing embedded liposomes, and methods for their formation and use. Through phagocytosis, monocytes infiltrating the matrix selectively incorporate the liposomes and their contents. The matrices may be injectable or implantable.

In exemplary embodiments, liposomes are introduced to a matrix (hydrogel) and are embedded in the matrix. The matrix can include one or more agents for recruiting cells (e.g., monocytes) to the matrix. Liposomes may be incubated with agents before being contacted with a matrix of the invention in some embodiments. In some embodiments, a matrix of the invention is formulated to incorporate agents and compounds that exert one or more effects upon cells which infiltrate the matrix. In other embodiments, a matrix of the invention is formulated to incorporate agents and compounds that attract cells (e.g., monocytes) to the matrix. In additional embodiments, the matrix is permeable to compounds produced by infiltrating cells. Compounds produced or secreted by cells within a matrix may diffuse out of the matrix and create effects in the surrounding environment in some embodiments. Additional embodiments of the invention include kits comprising a matrix of the invention and instructions for practicing the invention. In some embodiments, a kit of the invention includes matrix and one or more reagents for preparing liposomes for incorporation therein.

One embodiment of the invention features an implantable, semi-solid matrix comprising a hydrogel material and liposomes embedded therein. In particular embodiments, the matrix contains one or more agents useful in recruiting cells, e.g., monocytic cells, to a site of implantation. In other embodiments, the liposomes embedded in the matrix contain one or more agents which modify or modulate a behavior of monocytic cells. The behavior modified or modulated in this manner includes, but is not limited to, secretion of products produced by monocytic cells. The behavior or phenotype of monocytes may be modulated to achieve a particular therapeutic result.

For example, modulating the behavior or phenotype of monocytes at a specific location within a tissue can be used to deliver therapeutic proteins secreted from monocytes to the tissue. In one embodiment, this approach may be used to induce angiogenesis. Tissues and body parts can become damaged for a variety of different reasons. These include, but are not limited to a chronic disease such as autoimmune disorders, diabetes or atherosclerosis, or an acute event such as injury, trauma or an occlusive vascular event resulting in tissue injury due to ischemia. All of these conditions may result in loss of tissue function. Regeneration of injured or lost tissue can be achieved by several means, including replacing the damaged tissue with healthy tissue (such as by surgical tissue flap), by delivering stem cells or progenitor cells that will differentiate into new functional tissue, by enhancing circulation through the growth of new blood vessels in the tissue, and/or by mobilization of cells, oxygen and nutrients to the tissue thereby enhancing its regeneration. In order to facilitate regeneration, it is desirable to recruit cells within a patient's body to perform in a manner that will enhance regeneration of a damaged tissue or act to heal a damaged tissue. Such treatment can be achieved, for example, by manipulating cells in a specific location to act towards the growth of new blood vessels by secreting angiogenic factors, including but not limited to vascular endothelial growth factor. In another embodiment the invention can be used to differentiate stem cells or progenitor cells to specific cell types in a specific location in the body in order to regenerate tissue function.

In another embodiment, modulating the behavior or phenotype of monocytes at a specific location within a tissue can be used to trigger an immune response against an antigen presented by dendritic cells that differentiated from monocytes. Monocytes may differentiate into antigen-presenting dendritic cells upon exposure to antigen and/or exposure to factors that induce differentiation to a dendritic phenotype. In preferred embodiments, the antigen is a tumor antigen. Upon exposure to an antigen, e.g., a tumor antigen, monocytes can differentiate into dendritic cells that display the antigen on the cell surface. The dendritic cells can then activate T-cells with which they come into contact, triggering a cell-mediated immune response against the antigen. If the antigen is a tumor antigen, the cell-mediated immune response is directed against the antigens present in a tumor mass, effectively activating an immune response against the tumor. Antigens, including tumor antigens, can be delivered to monocytes by encapsulating the antigens inside liposomes and embedding them in a matrix, as described herein. Additional agents or factors can promote differentiation of monocytes to dendritic cells. These factors can be presented to monocytes separately or in combination with an antigen. In some embodiments, these agents include, but are not limited to, granulocyte-macrophage colony-stimulating factor, interleukin-4, TNFα, interleukin-15 and others. In some embodiments, these agents are delivered within the liposomes together with the tumor antigens to induce differentiation of monocytes to dendritic cells. In particular embodiments, the differentiation agents and the tumor antigens are contained within the same liposomes. In other embodiments, the differentiation agents and the tumor antigens are contained within separate liposomes embedded in the same matrix. Factors involved in the differentiation of monocytes to dendritic cells can also be incorporated within the hydrogel. Accordingly, in another embodiment, liposomes containing tumor antigens can be embedded in a hydrogel matrix containing one or more agents involved in differentiation of monocytes to dendritic cells, e.g., granulocyte-macrophage colony-stimulating factor, interleukin-4, TNFα, and interleukin-15. Additional factors involved in the differentiation of monocytes to dendritic cells are further described in Sabrina Mariotti et al, The FASEB Journal. 2008; 22:3370-3379, Suresh Kumar, Robert Jack, Journal of Endotoxin Research, Vol. 12, No. 5, 278-284 (2006) and S. Nagaraj et al, Indian J Med Res 119, April 2004, pp 133-138 incorporated herein by reference in its entirety.

In another embodiment, modulating the behavior or phenotype of monocytes at a specific location within a tissue can be used to deliver therapeutic proteins secreted from monocytes to the tissue. The compositions and methods of the invention can be used to differentiate stem cells or progenitor cells to specific cell types in a specific location in the body in order to regenerate tissue function. For example, the compositions and methods of the invention can be used to change a cell from one type to another (reprogramming) in order to overcome a shortage in specific cells, such as insulin-secreting beta cells.

Monocytes may be isolated from an individual and manipulated in vitro to achieve a desired phenotype. Such monocytes can then be delivered to a tissue by injection. Alternatively, if localization of delivery is desired, monocytes can by delivered by embedding them within a biocompatible matrix such as collagen or hyaluronic acid. In both instances autologous or allogeneic monocytes can be used.

Alternatively, endogenous monocytes can be manipulated to concentrate in specific locations in the body. As monocytes by nature of their function invade foreign objects, delivery of a foreign object in the form of a matrix (e.g., a matrix comprising collagen) will result in monocyte infiltration. The tendency of monocytes to infiltrate matrices in vivo can be used in order to differentiate these monocytes within the matrix by loading the matrix with specific molecules that direct the specific differentiation of monocytes. This method offers the advantage of using endogenous cells, eliminating the risk of immune response towards foreign cells and avoiding the need to draw blood and achieve differentiation in vitro.

In order to allow the differentiation of endogenous monocytes in the delivered matrix, the matrix should be loaded with compounds which stimulate or promote differentiation. Unless the compounds used for monocyte differentiation are coupled to, or embedded in the matrix material they will freely diffuse from the matrix and disperse in the tissue in which the matrix is embedded, resulting in a rapid decline in the concentration of the compounds within the matrix.

Monocytes are phagocytic cells, which use phagocytosis as means for incorporating foreign objects, bacteria and debris. Monocyte phagocytosis is used in order to deliver compounds and drugs to monocytes by encapsulating the delivered compound in a liposome and injecting the liposome suspension into the blood circulation. Through phagocytosis, monocytes selectively incorporate the liposomes and their content. Monocytes can be selectively targeted over other leucocytes by manipulating liposome size. Optimal liposome sizes for targeting monocytes range between, e.g., 20 nm and 1000 nm, 20 nm and 900 nm, 20 nm and 800 nm, 20 nm and 700 nm, 20 nm and 600 nm, 20 nm and 500 nm, or 25 nm and 400 nm. In preferred embodiments, optimal liposome size ranges between 50 nm and 300 nm, more preferably between 75 nm and 250 nm, and most preferably between 100 nm and 200 nm.

By incorporating liposomes containing specific compounds inside a semisolid matrix comprising a hydrogel material such as collagen or hyaluronic acid it is possible to achieve local delivery of liposomes to cells to control the cells' behavior. Accordingly, the use of liposomes embedded in a semisolid matrix is an advantageous means of achieving specific delivery of desired compounds to phagocitic cells such as monocytes and macrophages as well other endogenous cell derived from monocytes such as dendritic cells. Neutrophils can also phagocytose liposomes, but mainly participate in phagocytosis of antibody and complement coated antigens. Monocytes that invade a liposome-embedded semisolid matrix encounter liposomes and incorporate the liposome contents through phagocytosis. The liposomes hold desired compounds within the matrix, reducing the diffusion of the compounds from the matrix to the tissue. The specific phagocytic nature of monocytes will typically result in specific delivery to monocytes, although neutrophils may also perform phagocytosis but mainly of antibody and complement coated antigens. Liposomes can be targeted to monocytes and macrophages by making the liposome size range between 100 nm and 200 nm, although monocytes can phagocyte smaller as well as larger liposomes as well, e.g., liposomes between 25 nm and 400 nm.

As there is no diffusion of compounds from liposomes, the amount or dosage of compounds within the liposomes, and consequently within the tissue into which the liposome matrix is introduced, will remain constant. A common problem of matrix based delivery systems is the diffusion of compounds embedded in the matrix into the surrounding tissue, changing the concentration of the compound in the matrix and affecting its bioactivity. Contents contained within liposomes will be trapped within the liposomes and, consequently, trapped within the matrix, thereby allowing the contents to interact only with phagocytic cells, e.g., monocytes, infiltrating the matrix.

When a desired compound is embedded within the matrix, any cell having contact with the matrix is affected by the compound. The contents of liposomes are typically available only to phagocytic cells such as monocytes. However, liposomes can be targeted to other cells by specific targeting molecules such as antibodies or peptides placed on the liposome surface, thereby allowing the contents of the liposomes to be specifically targeted to particular cell types, minimizing the effect of the contents on cells not targeted for treatment.

This method will allow the differentiation of endogenous monocytes into different phenotypes or to reprogramming to different functional cells based on the desired function and therapeutic outcome.

V. Induction of an Angiogenic Phenotype

Control over the behavior of cells in a specific location in the body can be used for the treatment of different indications such as ischemia where a tissue is suffering from insufficient circulation resulting in cell being starved or in low supply of oxygen. As a result of this condition, cells may lose function or die. Increasing the production of angiogenic signals within the ischemic tissue that promote growth of blood vessels can help increase local circulation, help regenerate the tissue, and decrease ischemia. To achieve this goal one embodiment of the present invention describes materials and methods for the creation of a hydrogel embedded with liposomes that carry a bioactive compound that changes cellular behavior. By delivering the liposome embedded hydrogel to the ischemic tissue, monocytic cells that infiltrate the matrix incorporate the matrix embedded liposome containing the bioactive material and as result act to promote angiogenesis.

The methods and compositions of the invention may be used to induce an angiogenic phenotype in monocytes. This can be used to treat limb ischemia, wound healing, and other conditions associated with poor circulation. For example, a liposome matrix containing molecules that induce an angiogenic phenotype in monocytes can be delivered to a muscle tissue, or to connective tissues, internal organs, and spaces between tissues. Induction of an angiogenic phenotype in monocytes may be achieved by implanting in a tissue a permeable semisolid matrix embedded with liposomes containing adenosine (a trigger for monocyte differentiation into the angiogenic phenotype). Matrix infiltrating monocytes will adopt an angiogenic phenotype and will secrete vascular growth factors to promote the creation of new blood vessels and improve the circulation of the surrounding tissue.

The present invention features methods and compositions for endogenous cell therapy which employ an implantable matrix embedded with liposomes. Through phagocytosis, monocytic cells, e.g. monocytes, infiltrating the matrix selectively incorporate the liposomes and their contents. Accordingly, by incorporating liposomes containing specific compounds inside an implantable matrix, it is possible to deliver compounds to monocytes and modulate monocyte behavior.

In one aspect, the invention provides an implantable, semisolid matrix comprising a hydrogel material and liposomes embedded therein, wherein the liposomes contain at least one bioactive material, and wherein the matrix is permeable to the infiltration of cells from an implantation environment and to products secreted from the cells into the environment. In one embodiment of this aspect, the bioactive material is selected from the group consisting of a protein, a peptide, a nucleotide, a DNA, a RNA, a siRNA, and a cDNA, or a combination thereof. In another embodiment, the bioactive material is a small molecule, a drug or a combination thereof. In another embodiment, the liposomes contain more than one bioactive material. In an exemplary embodiment, the more than one bioactive materials include a biological and a chemical material.

In another embodiment of this aspect, the liposomes carry the material in the liposomal hydrophilic core, in the membrane on its surface or in a combination thereof. In yet another embodiment, the hydrogel contains a biological or chemical compound that is not carried within the liposomes. In one embodiment, the biological or chemical compound is a chemoattractant protein. In another embodiment, the chemoattractant protein is monocyte chemotactic protein-1.

In one embodiment, the liposomes are attached to the hydrogel matrix by a chemical bond, e.g., a peptide bond or an ionic bond. In another embodiment, the hydrogel material contain cells added to the hydrogel material prior to its implantation in the body. In one embodiment, the cells are monocytes.

In another embodiment, the hydrogel of the matrix comprises copolymers of two or more polyhydroxy acids, polyorthoesters, polyanhydrides, gelatin, collagen, cellulose, derivatized cellulose, chitosan, alginate, hyaluronan, thiol-modified hyaluronan, and combinations or copolymers thereof. In one embodiment, the polyhydroxy acid is polylactic acid, polyglycolic acid or other polyhydroxy acid.

In one embodiment, the matrix further comprises a cross-linking agent. In one embodiment, the cross-linking agent is glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, or tripolyphosphate, or combinations thereof.

In another aspect, the invention features a method for programming an implantable, semisolid matrix comprising a hydrogel material and liposomes embedded therein to affect the behavior of cell, comprising formulating within the liposomes a compound capable of affecting the cell's behavior, such that the cell infiltrates the semisolid matrix comprising the hydrogel material and takes up the liposomes through phagocytosis or through fusion of the liposome membrane with the cell membrane.

In another aspect, the invention features a method for affecting the behavior of a cell at or near a site of implantation in a subject, comprising implanting at the site an implantable, semisolid matrix comprising a hydrogel material and liposomes embedded therein, wherein the liposomes comprise at least one compound capable of affecting the cell's behavior, such that the cell infiltrates the semisolid matrix comprising the hydrogel material and takes up the liposomes through phagocytosis or through fusion of the liposome membrane with the cell membrane. In various embodiments, the behavior is an angiogenic activity, an immunosuppressive activity, or an inflammatory activity. In certain embodiments, the cell is a monocytic cell, e.g., a monocyte or a macrophage. In an exemplary embodiment, the monocytic cell secretes vascular growth factors at or near the implantation site. In exemplary embodiments, the compound contained within the liposomes is adenosine, IL-4, IL-10, or combinations thereof. In other embodiments, the compound contained within the liposomes is IL-10, IL-4, IL-13, an IL-1 receptor ligand, PGE2, TGF-β, TNFα, lactic acid, lipoteichoic acid, NADH dehydrogenase 5, subunit 1, poly(adenosine diphosphate-ribose) polymerase, pyruvate, Colony Stimulating Factor-1, adenosine, an adenosine analogue, NECA, LPS, Pam3CSK4, *E. coli* LPS, R848, imiquimod, non-methylated CpG DNA, ODN2006, thioredoxin peroxidase, Trapidil, TLR2 agonist (e.g., Pam3CysSerLys4, peptidoglycan (Ppg), PamCys), a TLR3 agonist (e.g., IPH 31XX), a TLR4 agonist (e.g., Aminoalkyl glucosaminide phosphates [ACPs], E6020, CRX-675, 5D24.D4, RC-527), a TLR7 agonist (e.g., Imiquimod, 3M-003, Aldara, 852A, R850, R848, CL097), a TLR8 agonist M-002), a TLR9 agonist (Flagellin, VaxImmune, CpG ODN (AVE0675, HYB2093), CYT005-15 AllQbG10, dSLIM), adenosine A1 agonists (R-PIA, CPA TCPA, CVT-3146, CVT-510, GR 79236, WAG 994), adenosine A2 agonists (CGS 21680, APEC, 2HE-NECA), and/or adenosine A3 agonists (e.g., IB-MECA, CI-IB-MECA, 3'-Aminoadenosine-5'-uronamides) and Alendronate, and combinations thereof.

In another aspect, the invention features a method for delivering a secreted product to a localized site in a subject comprising, providing at the localized site a liposome matrix composition described herein, and maintaining the matrix or composition at the localized site for a period of time sufficient for the secreted product to interact with the localized site. In one embodiment, the implantation site is within an ischemic tissue.

Additional embodiments of the invention feature an injectable composition comprising a hydrogel material and liposomes that are added to the injectable composition, where the liposomes include one or more agents which modify or modulate a behavior of monocytic cells. Such agents include, but are not limited to, nucleic acid molecules, polypeptides, and small molecule chemical compounds. In some embodiments, the material is a nucleotide, an expression vector, a cytokine, or a growth factor. In exemplary embodiments, the liposomes include one or more of the following: IL-10, IL-4, IL-13, an IL-1 receptor ligand, PGE2, TGF-β, TNFα, INFγ, lactic acid, lipoteichoic acid, NADH dehydrogenase 5, subunit 1, poly(adenosine diphosphate-ribose) polymerase, pyruvate, Colony Stimulating Factor-1, adenosine, an adenosine analogue, NECA, LPS, Pam3CSK4, E. coli LPS, R848, imiquimod, non-methylated CpG DNA, ODN2006, thioredoxin peroxidase, Trapidil, TLR2 agonist (e.g., Pam3CysSerLys4, peptidoglycan (Ppg), PamCys), a TLR3 agonist (e.g., IPH 31XX), a TLR4 agonist (e.g., Aminoalkyl glucosaminide phosphates [AGPs], E6020, CRX-675, 5D24.D4, RC-527), a TLR7 agonist (e.g., Imiquimod, 3M-003, Aldara, 852A, R850, R848, CL097), a TLR8 agonist (3M-002), a TLR9 agonist (Flagellin, VaxImmune, CpG ODN (AVE0675, HYB2093), CYT005-15 AllQbG10, dSLIM), adenosine A1 agonists (R-PIA, CPA TCPA, CVT-3146, CVT-510, GR 79236, WAG 994), adenosine A2 agonists (CGS 21680, APEC, 2HE-NECA), and/or adenosine A3 agonists (e.g., 1B-MECA, CI-IB-MECA, 3'-Aminoadenosine-5'-uronamides), and Alendronate. The injectable composition is convertible to a semi-solid state in some embodiments, and the injectable composition can be permeable to a product secreted by monocytic cells that infiltrate the composition. Some embodiments feature injectable compositions that can be converted to a semi-solid state by exposing the composition to heat, ionizing radiation or ultraviolet radiation. In some embodiments, infiltrating monocytic cells are capable of producing more than one product. In some embodiments, the product secreted is determined by the content of liposomes embedded within the injectable composition. In some embodiments, a product secreted by a monocytic cell is an angiogenic factor. Vascular endothelial growth factor (VEGF), fibroblast growth factor (FGF), platelet derived growth factor (PDGF), hepatocyte growth factor/scatter factor (HGF/SF), epidermal growth factor (EGF), and/or Interleukin-8 (TL-8) are secreted by a monocytic cell in some embodiments. A product secreted by a monocytic cell may be an immunosuppressive factor in some embodiments. A monocytic cell in some embodiments may secrete one or more immunosuppressive factors such as IL-4, IL-10 and/or TGF-β. In some embodiments, a monocytic cell may be a monocyte precursor cell and may be a bone marrow cell and/or a monocyte progenitor cell in some embodiments.

Aspects of the invention include a matrix comprising a hydrogel which may comprise one or more polymers. In some embodiments, the hydrogel comprises polylactic acid, polyglycolic acid, other polyhydroxy acids, copolymers of two or more polyhydroxy acids, polyorthoesters, polyanhydrides, gelatin, collagen, cellulose, derivatized cellulose, chitosan, alginate, thiol-modified hyaluronan, and/or combinations or copolymers thereof.

Cross-linkers are comprised by a matrix of the invention in some embodiments. In particular embodiments, a matrix of the invention comprises one or more of glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, tripolyphosphate, and combinations thereof.

Additional aspects of the invention include methods for recruiting cells (e.g., monocytes) to a localized site in a subject. In some embodiments, a method of the invention includes delivering a matrix containing liposomes (i.e., a liposome matrix) to a localized site and maintaining the matrix in the localized site for a period of time sufficient for cells, e.g., monocytes, to migrate to and/or infiltrate the localized site. In some embodiments of the invention, a subject that receives a matrix of the invention has a disease, has a condition and/or is at risk for a disease and/or a condition. In some embodiments, the disease and/or condition that a subject has or has a risk for is coronary artery disease, peripheral artery disease, limb ischemia, ischemic wound, ischemic ulcer, ischemic bowel disease, atherosclerotic ischemic disease, muscle flaps, skin flaps, organ transplant, nasolabial folds, wrinkles, conditions which result in scar formation, conditions requiring plastic surgery and/or conditions requiring a cosmetic procedure.

Some aspects of the invention feature a method for treating a subject that has or is at risk of having ischemia. In some embodiments, a matrix or composition of the invention is administered at a site of ischemia. In some embodiments, the administration of a matrix or composition results in recruitment of cells capable of secreting one or more angiogenic factors at the site for a time sufficient to prevent or lessen the effects of a perfusion injury associated with the ischemia. In some embodiments, a method for treating a subject that has or is at risk for cardiac ischemia is featured. In some embodiments, the method for administering the liposome matrix to a site is by injection.

Additional aspects of the invention include methods for reducing the nasolabial folds or wrinkles in a subject, comprising administering at the site of the nasolabial folds or wrinkles a matrix or composition of the invention, such that secretion of an angiogenic factor is effected for a time sufficient to detectably reduce the number and/or depth of the nasolabial folds or wrinkles. In some embodiments, a method for reducing the nasolabial folds or wrinkles in a subject comprises injecting a matrix or composition of the invention.

In some aspects of the invention, a method for reducing an immune response at a localized site in a subject is featured, wherein a matrix or composition of the invention is administered at a site and cells are recruited that are capable of secreting one or more immunosuppressive factors for a time sufficient to detectably reduce the immune response at the localized site. In some embodiments, a liposome-containing matrix or composition of the invention administered to reduce an immune response at a localized site in a subject is injected.

VI. Induction of an Immune Response Against Cancer Cells

A basic mechanism for fighting cancer cell growth in the body is the ability of the immune system to recognize the changes in cells that act in an abnormal manner and remove them. Rarely, the immune system fails to recognize a cancer cell as a problem, leading to the proliferation of the cancer cell and the development of a tumor. One strategy to fight such tumors is to help teach the immune system to recognize the tumor as a problem. To achieve this, target antigens from the tumor, from a similar tumor, or from synthetic peptides are presented to dendritic cells which in turn can elicit T cell-mediated tumor destruction. In one embodiment of the present invention, cancer antigens are encapsulated within liposomes alone or together with other bioactive materials such as an adjuvant. The liposomes are embedded within a hydrogel and placed in the area of the tumor by injection or implantation. Monocytes that infiltrate the matrix incorporate the liposomes by phagocytosis or by fusion of the liposomes with the monocytes membrane. The monocytes differentiate into dendritic cells that elicit a T cell-mediated response targeting the patients tumor.

The methods and compositions described herein may be used to induce an immune response against cancer cells. This approach can be used to treat cancer. In exemplary embodiments, a hydrogel containing liposomes can be delivered at or near the location of a tumor, but can also be delivered to connective tissues, internal organs, and spaces between tissues that are not directly in contact with the tumor. Induction of an immune response by monocytes may be achieved by implanting in a tissue a permeable semisolid matrix embedded with liposomes containing cancer antigens from a patient or cancer cells or antigens that were produced not from a patient's cells but can induce specific reaction against the patient's cancer cells. Matrix infiltrated monocytes can differentiate into dendritic cells and can interact with T cells to induce a cytotoxic reaction against the cancer cells. The dendritic cells are released from the matrix following the degradation of the matrix or by active migration, enabling their interaction with T cells and B cells, and the induction of a specific anti cancer immune response.

The present invention features methods and compositions for endogenous cell therapy which employ an implantable matrix embedded with liposomes. Through phagocytosis, monocytic cells, e.g. monocytes, infiltrating the matrix selectively incorporate the liposomes and their contents. Accordingly, by incorporating liposomes containing specific compounds inside an implantable matrix, it is possible to deliver compounds to monocytes and modulate monocyte behavior.

In one aspect, the invention provides an implantable, semisolid matrix comprising a hydrogel material and liposomes embedded therein, wherein the liposomes contain at least one bioactive material, and wherein the matrix is permeable to the infiltration of cells from an implantation environment and to products secreted from the cells into the environment. In one embodiment of this aspect, the bioactive material is selected from the group consisting of a protein, a peptide, a nucleotide, a DNA, a RNA, a siRNA, and a cDNA, or a combination thereof. In another embodiment, the bioactive material is a small molecule, a drug or a combination thereof. In another embodiment, the liposomes contain more than one bioactive material. In an exemplary embodiment, the more than one bioactive materials include a biological and a chemical material.

In another embodiment of this aspect, the liposomes carry the material in the liposomal hydrophilic core, in the membrane on its surface or in a combination thereof. In yet another embodiment, the hydrogel contains a biological or chemical compound that is not carried within the liposomes. In one embodiment, the biological or chemical compound is a chemoattractant protein. In another embodiment, the chemoattractant protein is monocyte chemotactic protein-1.

In one embodiment, the liposomes are attached to the hydrogel matrix by a chemical bond, e.g., a peptide bond or an ionic bond. In another embodiment, the hydrogel material contain cells added to the hydrogel material prior to its implantation in the body. In one embodiment, the cells are monocytes.

In another embodiment, the hydrogel of the matrix comprises copolymers of two or more polyhydroxy acids, polyorthoesters, polyanhydrides, gelatin, collagen, cellulose, derivatized cellulose, chitosan, alginate, hyaluronan, thiol-modified hyaluronan, and combinations or copolymers thereof. In one embodiment, the polyhydroxy acid is polylactic acid, polyglycolic acid or other polyhydroxy acid.

In one embodiment, the matrix further comprises a cross-linking agent. In one embodiment, the cross-linking agent is glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, or tripolyphosphate, or combinations thereof.

In another aspect, the invention features a method for programming an implantable, semisolid matrix comprising a hydrogel material and liposomes embedded therein to affect the behavior of cell, comprising formulating within the liposomes a compound capable of affecting the cell's behavior, such that the cell infiltrates the semisolid matrix comprising the hydrogel material and takes up the liposomes through phagocytosis or through fusion of the liposome membrane with the cell membrane.

In another aspect, the invention features a method for effecting the behavior of a cell at or near a site of implantation in a subject, comprising implanting at the site an implantable, semisolid matrix comprising a hydrogel material and liposomes embedded therein, wherein the liposomes comprise at least one compound capable of affecting the cell's behavior, such that the cell infiltrates the semisolid matrix comprising the hydrogel material and takes up the liposomes through phagocytosis or through fusion of the liposome membrane with the cell membrane. In one embodiment of this aspect, the behavior is an antigen presenting activity. In an exemplary embodiment, the cell is a monocyte, and the compound is a tumor antigen. In one embodiment, the tumor antigen is derived from tumor cells or tumor tissue from the subject. In another embodiment, the tumor antigen In one embodiment, the monocyte displays a tumor antigen for recognition by a T cell and/or a B cell at or near the implantation site.

In another aspect, the invention features a method for presenting a tumor antigen at a localized site in a subject comprising, providing at the localized site an implantable, semisolid matrix comprising a hydrogel material and liposomes embedded therein, wherein the liposomes comprise the tumor antigen and maintaining the matrix or composition at the localized site for a period of time sufficient for a phagocytic cell to infiltrate the matrix, phagocytose the antigen and present the antigen to an immune cell at the localized site. In one embodiment, the localized site is at or near a tumor site, such that an immune response to the tumor is enhanced.

One embodiment of the invention features an implantable, semi-solid matrix comprising a hydrogel material and liposomes embedded therein. In particular embodiments, the matrix contains one or more agents useful in recruiting cells, e.g., monocytic cells, to a site of implantation. In other embodiments, the liposomes embedded in the matrix contain one or more agents which modify or modulate a behavior of monocytic cells. The behavior modified or modulated in this manner includes, but is not limited to, secretion of products produced by monocytic cells, antigen presentation by monocytic cells, differentiation into dendritic cells, and migration of cells or release of cells from the matrix followed by direct interaction of the monocytic cells with other effector cells such as T cells and B cells. One of the key roles of monocytes in the immune system is to act as precursors for dendritic cells. Dendritic cells are derived from hemopoietic stem cells through either the common lymphoid or the common myeloid progenitor pathways. Mo-DC or MDDC refers to dendritic cells matured from monocytes. HP-DC refers to dendritic cells derived from hematopoietic progenitor cells. Dendritic cells act as antigen presenting cells for other effector cells of the immune system such as T cells. The compositions and methods described herein can be used to promote the differentiation of monocytes into dendritic cells. The dendritic cells can then be used in cell therapy, including in the treatment of cancer. Dendritic cell-based therapy is described in S. Nagaraj et al, Indian J Med Res 119, April 2004, pp 133-138, and in M Jefford a, E Maraskovsky b, J Cebon c, I D Davis d. The use of dendritic cells in cancer therapy. The Lancet Oncology, Volume 2, Issue 6, Pages 343-353, June 2001, the entire contents of which are incorporated herein by reference.

In exemplary embodiments, liposomes embedded in the hydrogel matrix of the invention contain one or more tumor antigens. In preferred embodiments, the tumor antigens are polypeptide molecules. In other embodiments, the tumor antigens are encoded by nucleic acid molecules embedded within the liposomes. The tumor antigens may be autologous, allogeneic, or syngeneic. In an exemplary embodiment, the tumor antigens are obtained from a tumor sample or biopsy obtained from a patient. Following implantation of the liposome matrix in a subject, circulating monocytic cells, e.g., monocytes, will infiltrate the matrix and will phagocytose liposomes containing the tumor antigens. In an exemplary embodiment, the subject is the same subject from whom the tumor antigens were obtained. After phagocytosis of the liposomes containing the tumor antigens, the monocytic cells differentiate into dendritic cells which activate T-cells in their environment. Activation of T-cells triggers a cell-mediated immune response targeted to attack the antigens contained within the liposomes. If the antigens are tumor antigens, the cell-mediated immune response is targeted to attack a tumor containing the tumor antigens. Antigen-presenting dendritic cells can also trigger activation of B-cells, stimulating a B-cell response against a tumor.

In other exemplary embodiments, the liposomes embedded in the hydrogel matrix of the invention contain one or more agents or factors involved in differentiation of monocytes to dendritic cells. In some embodiments, these agents include, but are not limited to, granulocyte-macrophage colony-stimulating factor, interleukin-4, TNFα, interleukin-15 and others. In some embodiments, these agents are delivered within the liposomes together with the tumor antigens to induce differentiation of monocytes to dendritic cells. In particular embodiments, the differentiation agents and the tumor antigens are contained within the same liposomes. In other embodiments, the differentiation agents and the tumor antigens are contained within separate liposomes embedded in the same matrix. Factors involved it the differentiation of monocytes to dendritic cells can be incorporated within the hydrogel. Accordingly, in another embodiment, liposomes containing tumor antigens can be embedded in a hydrogel matrix containing one or more agents involved in differentiation of monocytes to dendritic cells, e.g., granulocyte-macrophage colony-stimulating factor, interleukin-4, TNFα, and interleukin-15. Additional factors involved in the differentiation of monocytes to dendritic cells are further described in Sabrina Mariotti et al, The FASEB Journal. 2008; 22:3370-3379, Suresh Kumar, Robert Jack, Journal of Endotoxin Research, Vol. 12, No. 5, 278-284 (2006) and S. Nagaraj et al, Indian J Med Res 119, April 2004, pp 133-138 incorporated herein by reference in its entirety.

Tumor antigens for inclusion in liposomes may be prepared by any method known in the art suitable for preparing tumor antigens. Such methods include methods for extracting and/or purifying polypeptides from a cell or tissue sample, recombinant proteins and tumor associated antigens. Particular methods for preparing tumor antigens from autologous, allogeneic, syngeneic and other sources are described in the following references, incorporated herein by reference in their entireties:

1. Christopher P. Tarassoff, Philip M. Arlen, James L. Gulley. Therapeutic Vaccines for Prostate Cancer. The Oncologist, Vol. 11, No. 5, 451-462, May 2006; doi: 10.1634/theoncologist.11-5-451
2. Morse M A, Lyerly H K, Gilboa E, Thomas E, Nair S K. Optimization of the sequence of antigen loading and CD40-ligand-induced maturation of dendritic cells. Cancer Res. 1998; 58:2965-2968.
3. Mosca P J, Hobeika A C, Clay T M, et al. A subset of human monocyte-derived dendritic cells expresses high levels of interleukin-12 in response to combined CD40 ligand and interferon-gamma treatment. Blood. 2000; 96:3499-3504.
4. Morse M A, Coleman R E, Akabani G, Niehaus N, Coleman D, Lyerly H K. Migration of human dendritic cells after injection in patients with metastatic malignancies. Cancer Res. 1999; 59:56-58.
5. Morse M A, Deng Y, Coleman D, Hull S, et al. A Phase I study of active immunotherapy with carcinoembryonic antigen peptide (CAP-1)-pulsed, autologous human cultured dendritic cells in patients with metastatic malignancies expressing carcinoembryonic antigen. Clin Cancer Res. 1999; 5:1331-1338.
6. Li Y, Bendandi M, Deng Y, et al. Tumor-specific recognition of human myeloma cells by idiotype-induced CD8+ T cells. Blood. 2000; 96:2828-2833.
7. Banchereau J, Palucka A K, Dhodapkar M, et al. Immune and clinical responses in patients with metastatic melanoma to CD34+ progenitor-derived dendritic cell Vaccine. Cancer Res. 2001; 61:6451-6458.
8. Sadanga N, Nagashima H, Mashino K, et al. Dendritic cell vaccination with MAGE peptide is a novel therapeutic approach for gastrointestinal carcinomas. Clin Cancer Res. 2001; 7:2277-2284.
9. Fong L, Hou Y, Rivas A, et al. Altered peptide ligand vaccination with Flt3 ligand expanded dendritic cells for tumor immunotherapy. Proc Natl Acad Sci USA. 2001; 98:8809-8814.
10. Toungouz M, Libin M, Bulte F, et al. Transient expansion of peptide-specific lymphocytes producing IFN-gamma after vaccination with dendritic cells pulsed with MAGE peptides in patients with MAGE-A1/A3-positive tumors. J Leukoc Biol. 2001; 69:937-943.
11. Rains N, Cannan R F, Chen W, Stubbs R S. Development of a dendritic cell (DC)-based vaccine for patients with advanced colorectal cancer. Hepatogastroenterology. 2001; 48:347-351.

12. Fong L, Brockstedt D, Benike C, Wu L, Engleman E G. Dendritic cells injected via different routes induce immunity in cancer patients. J. Immunol. 2001; 166:4254-4259.
13. Yu J S, Wheeler C J, Zeltzer P M, et al. Vaccination of malignant gliomas patients with peptide-pulsed dendritic cells elicits systemic cytotoxicity and intracranial T cell infiltration. Cancer Res. 2001:61:842-847.
14. Nishiyama T, Tachibana M, Horiguchi Y, et al. Immunotherapy of bladder cancer using autologous dendritic cells pulsed with human lymphocyte antigen-A24-specific MAGE-2 peptide. Clin Cancer Res. 2001; 7:23-31.
15. Small E J, Fratesi P, Reese D M, et al. Immunotherapy of hormone-refractory prostate cancer with antigen-loaded dendritic cells. J Clin Oncol. 2000; 18:3894-3903.
16. Schuler-Thurner B, Dieckmann D, Keikavoussi P, et al. Mage-3 and influenza-matrix peptide-specific cytotoxic T cells are inducible in terminal stage HLA-A2.1+ melanoma. *J Immunol.* 2000 Sep. 15; 165(6):3492-6.
17. M Jefford a, E Maraskovsky b, J Cebon c, ID Davis d. The use of dendritic cells in cancer therapy. The Lancet Oncology, Volume 2, Issue 6, Pages 343-353, June 2001.

The injectable liposome matrix composition is convertible to a semi-solid state in some embodiments, and the injectable composition can be permeable to a product secreted by monocytic cells that infiltrate the composition and can allow for monocytic and dendritic cells to be released from the composition by migration or by degradation of the composition. Some embodiments feature injectable compositions that can be converted to a semi-solid state by exposing the composition to heat, ionizing radiation or ultraviolet radiation. In some embodiments, infiltrating monocytic cells are capable of producing more than one product. In some embodiments, the product secreted is determined by the content of liposomes embedded within the injectable composition. In some embodiments, a monocytic cell may be a monocyte precursor cell and may be a bone marrow cell and/or a monocyte progenitor cell.

Aspects of the invention include a matrix comprising a hydrogel which may comprise one or more polymers. In some embodiments, the hydrogel comprises polylactic acid, polyglycolic acid, other polyhydroxy acids, copolymers of two or more polyhydroxy acids, polyorthoesters, polyanhydrides, gelatin, collagen, cellulose, derivatized cellulose, chitosan, alginate, thiol-modified hyaluronan, and/or combinations or copolymers thereof.

Cross-linkers are comprised by a matrix of the invention in some embodiments. In particular embodiments, a matrix of the invention comprises one or more of glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, tripolyphosphate, and combinations thereof.

Additional aspects of the invention include methods for recruiting cells (e.g., monocytes) to a localized site in a subject. In some embodiments, a method of the invention includes delivering a matrix containing liposomes (i.e., a liposome matrix) to a localized site and maintaining the matrix in the localized site for a period of time sufficient for cells, e.g., monocytes, to migrate to and/or infiltrate the localized site. In some embodiments of the invention, a subject that receives a matrix of the invention has a disease, has a condition and/or is at risk for a disease and/or a condition. The disease and/or condition that a subject has or has a risk for is cancer.

Some aspects of the invention feature a method for treating a subject that has or is at risk of having cancer. In some embodiments, a matrix or composition of the invention is administered at or near a site of a tumor. In some embodiments, the administration of a matrix or composition results in recruitment of cells capable of mediating and promoting a cytotoxic response against tumor cells or against monocyte derived dendrcitc cells. In some embodiments, the method for administering the liposome matrix to a site is by injection.

VII. Induction of Cell Reprogramming

The loss of specific cell function due to a disease or disorder such as an autoimmune disease, injury, or a genetic defect can have far reaching implications in patients, such as, for example, in the cases of diabetes and Parkinson's disease. In diabetes, the loss of insulin producing beta cells can lead to high glucose levels and multiple damage to cells, tissues, and organs; whereas in Parkinson's disease, the losso of dopamine-producing cells can lead to dopamine deficiency, expressed as loss of motor function.

One strategy for treating these conditions is by compensating for the loss of cell function by delivering the necessary molecules directly to a subject, such as in the case of diabetes where insulin is injected directly to the blood. In the case of Parkinson's disease, the dopamine precursor L-DOPA is administered to subjects, since dopamine itself does not cross the blood-brain barrier.

The permanent need for insulin in diabetes patients, and for dopamine in Parkinson's disease patients, makes treatment by administration of the necessary molecules inconvenient and less than optimally effective.

A treatment that will result in replacing the lost cell function with functioning cells that will supply the body with the lost protein, e.g., a hormone or a neurotransmitter, is more effective and provides greater therapeutic benefits to a patient's health and quality of life.

Adult cell reprogramming is the concept of transforming cells from one specific subset into a different subset. Such reprogramming can be, for example, turning skin fibroblasts into undifferentiated stem cells with the potential to differentiate into many different cell types, or the reprogramming of skin fibroblasts into a different cell type, such as insulin secreting beta cells, without turning the skin fibroblast into an undifferentiated stem cell.

Different transcription factors have been described which are involved in cell reprogramming. Reprogramming somatic cells to a pluripotent embryonic state involves key transcription factors, including, for example, Oct4, Sox2, c-Myc, klf-4 and Nanog. These factors, together with Polycomb group (PcG) proteins, regulate other transcription factors important for cell differentiation. Transcription factors useful for reprogramming ectoderm include, for example, PAX6, MEIS1, and OTX1. Transcription factors useful for reprogramming endoderm include, for example, ATBF1. Transcription factors useful for reprogramming mesoderm include, for example, DLX5, HAND1, and OENCUT1.

The present invention is based, at least in part, on the discovery that monocytes can be reprogrammed to other cell types that have therapeutic utility in treatment of diseases. For example, monocytes can be reprogrammed to become insulin-secreting beta cells, or dopamine producing cells.

Monocytes are a type of leukocyte, or white blood cell, which have an integral role in the innate immune system. Following the appearance of signals delivered from a specific site in the body, monocytes are mobilized by chemotactic signals and adhere to the activated endothelium through interactions mediated by adhesion molecules including P-CAM, V-CAM and I-CAM on endothelial cells and CD18 and CD11B on monocytes. Following their adhesion to the endothelium, monocytes transmigrate into the tissue and differentiate into macrophages.

Together with neutrophils, eosinophils and natural killer cells, monocytes function as a first-line defense to detect, eliminate or contain invading microbes and toxic macromolecules. Monocytes responses towards these targets are rapid and triggered by structures, commonly referred to as Pathogen-Associated Molecular Patterns (PAMP). Whenever the innate immunity is unable to handle an invading microorganism, monocytes function as effector cells of the adaptive immune system, after receiving the appropriate activation and information from antigen-specific T and B-lymphocytes.

Monocytes also have essential functions in wound healing and resolution of inflammation, mediating cell migration, extra-cellular matrix remodeling and angiogenesis, all of which are required for tissue repair.

Consequently, an ultimate goal of monocytes is the maintenance of tissue homeostasis and integrity. This is achieved by various monocyte functions, such as, secretion of specific proteins, scavenging, elimination of pathogen and tumor cells, clearance of senescent cells, control of tissue cell growth and modulation of the extra-cellular milieu.

To accomplish these tasks, monocytes exhibit a highly flexible gene expression program that allows them to adapt and respond to changes in their surrounding micro-environment, as well as to recruit, engage and coordinate other cell types in restoring normal tissue structure and function. These various monocyte activities are not displayed concomitantly and, in fact, some of these activities are clearly contradictory (e.g., degradation versus synthesis of extra-cellular matrix). Thus, tissue monocytes are functionally heterogeneous under basal conditions, and exhibit a large degree of variability upon activation by endogenous factors or exogenous stimuli (see Vega, M A et al, Immunologia 2006, 25(4): 248-272).

Monocyte implantation at site of ischemic tissue has been attempted as a therapeutic approach for the treatment of various conditions such as cancer, heart disease, ischemia, nerve injury, wound healing and diabetes. Similarly, monocyte therapy has been used for the delivery of therapeutic proteins by genetic manipulation, activation or transformation of the monocytes (Muhlebach, M. D., et al., Mol Ther, 2005. 12:1206-16; Lu, Y., et al., Cell Mol Biol, 2003. 49:1151-6; Spiekermann, K., et al., Eur J Haematol, 2001. 67:63-71; US 2006/0257359). The use of monocytes has also been described for nerve repair and spinal cord injury treatment (Lazarov-Spiegler, O., Solomon, A. S., and Schwartz, M. Glia, 1998. 24:329-37; Rapalino, O., et al., Nat Med, 1998. 4:814-21; Schwartz, M., et al., Neurosurgery, 1999. 44:1041-6; U.S. Pat. No. 6,267,955).

While some progress has been made in the field of cellular therapy and therapeutic protein delivery for tissue repair, there exists a need to improve the ability to manipulate monocyte behavior in vivo.

The present invention is based on the development of compositions and methods for delivery of compounds encapsulated in liposomes. Embodiments of the invention feature liquid, semi-solid and solid matrices containing embedded liposomes, and methods for their formation and use. Through phagocytosis, monocytes infiltrating the matrix selectively incorporate the liposomes and their contents. The matrices may be injectable or implantable.

In exemplary embodiments, liposomes are introduced to a matrix (hydrogel) and are embedded in the matrix. The matrix can include one or more agents for recruiting cells (e.g., monocytes) to the matrix. Liposomes may be incubated with agents before being contacted with a matrix of the invention in some embodiments. In some embodiments, a matrix of the invention is formulated to incorporate agents and compounds that exert one or more effects upon cells which infiltrate the matrix. In other embodiments, a matrix of the invention is formulated to incorporate agents and compounds that attract cells (e.g., monocytes) to the matrix. In additional embodiments, the matrix is permeable to compounds produced by infiltrating cells. Compounds produced or secreted by cells within a matrix may diffuse out of the matrix and create effects in the surrounding environment in some embodiments. Additional embodiments of the invention include kits comprising a matrix of the invention and instructions for practicing the invention. In some embodiments, a kit of the invention includes matrix and one or more reagents for preparing liposomes for incorporation therein.

One embodiment of the invention features an implantable, semi-solid matrix comprising a hydrogel material and liposomes embedded therein. In particular embodiments, the matrix contains one or more agents useful in recruiting cells, e.g., monocytic cells, to a site of implantation. In other embodiments, the liposomes embedded in the matrix contain one or more agents which modify or modulate a behavior of monocytic cells. The behavior modified or modulated in this manner includes, but is not limited to, secretion of products produced by monocytic cells.

Additional embodiments of the invention feature an injectable composition comprising a hydrogel material and liposomes that are added to the injectable composition, where the liposomes include one or more agents which modify or modulate a behavior of monocytic cells. Such material includes, but is not limited to, expression vectors encoding one or more transcription factors which function in differentiation and/or reprogramming of monocytic cells, e.g., monocytes. These transcription factors include, for example, Oct4, Sox2, c-Myc, klf-4, Nanog. Polycomb group (PcG) proteins, PAX6, MEIS1, OTX1, ATBF1, DLX5, HAND1, Nuclear factor kappa-B and OENCUT1. Additional transcription factors that can function in differentiation and/or reprogramming which may be incorporated in expression vectors encapsulated within liposomes are described in: Transcription Factors, Series: Handbook of Experimental Pharmacology, Vol. 166, by Manfred Gossen (Editor), Jörg Kaufmann (Editor), Steven J. Triezenberg (Editor), Springer, 2004, the entire contents of which are incorporated herein by reference. Following injection of the hydrogel composition, monocytic cells infiltrating the matrix can phagocytose the liposomes contained therein, thereby resulting in expression of the exogenous transcription factors, and differentiation or reprogramming into a cell type having altered phenotypic characteristics. In exemplary embodiments, the monocytic cells are reprogrammed into insulin-secreting beta cells or dopamine-producing cells.

The injectable composition is convertible to a semi-solid state in some embodiments, and the injectable composition can be permeable to a product secreted by monocytic cells that infiltrate the composition. Some embodiments feature injectable compositions that can be converted to a semi-solid state by exposing the composition to heat, ionizing radiation or ultraviolet radiation. In some embodiments, infiltrating monocytic cells are capable of producing more than one product. In some embodiments, the product secreted is determined by the content of liposomes embedded within the injectable composition. In some embodiments, a product secreted by a monocytic cell following reprogramming is insulin. In other embodiments, a product secreted by a monocytic cell following reprogramming is dopamine. In some embodiments, a monocytic cell may be a monocyte precursor cell and may be a bone marrow cell and/or a monocyte progenitor cell in some embodiments.

Aspects of the invention include a matrix comprising a hydrogel which may comprise one or more polymers. In some embodiments, the hydrogel comprises polylactic acid, polyglycolic acid, other polyhydroxy acids, copolymers of two or more polyhydroxy acids, polyorthoesters, polyanhydrides, gelatin, collagen, cellulose, derivatized cellulose, chitosan, alginate, thiol-modified hyaluronan, and/or combinations or copolymers thereof.

Cross-linkers are comprised by a matrix of the invention in some embodiments. In particular embodiments, a matrix of the invention comprises one or more of glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, tripolyphosphate, and combinations thereof.

Additional aspects of the invention include methods for recruiting cells (e.g., monocytes) to a localized site in a subject. In some embodiments, a method of the invention includes delivering a matrix containing liposomes (i.e., a liposome matrix) to a localized site and maintaining the matrix in the localized site for a period of time sufficient for cells, e.g., monocytes, to migrate to and/or infiltrate the localized site. In some embodiments of the invention, a subject that receives a matrix of the invention has a disease, has a condition and/or is at risk for a disease and/or a condition. In some embodiments, the disease and/or condition that a subject has or has a risk for is diabetes or Parkinson's disease.

Some aspects of the invention feature a method for treating a subject that has or is at risk of having diabetes or Parkinson's disease. In some embodiments, a matrix or composition of the invention is administered to the pancreas. In some embodiments, the administration of a matrix or composition results in recruitment of cells capable of secreting insulin for a time sufficient to prevent or lessen the effects of diabetes. In some embodiments, a method for treating a subject that has or is at risk for diabetes is featured. In other embodiments, a matrix or composition of the invention is administered to the brain. In some embodiments, the administration of a matrix or composition results in recruitment of cells capable of secreting dopamine for a time sufficient to prevent or lessen the effects of Parkinson's disease. In some embodiments, the method for administering the liposome matrix to a site is by injection.

In one embodiment, the present invention describes materials and methods for the local reprogramming of cells in a location where treatment is applied. The compositions and methods of the invention can be used to replace lost cells or lost cell function due to disease, injury or genetic defect. Compositions include a semisolid hydrogel matrix embedded with liposomes. The liposomes contain an effector molecule or molecules that can induce the reprogramming of cells. When phagocytic cells such as monocytes infiltrate the hydrogel following implantation into a subject, they encounter the liposomes and incorporate the liposomes carrying the effector molecules into the cells. The effector molecules can be genetic material encoding the expression of specific proteins such as transcription factors, the expression of which can initiate the reprogramming of the cell. The matrix can contain other effector molecules designed to attract specific cells to the matrix or to support the reprogramming process. The reprogrammed cells can be released from the matrix as the matrix degrades or by the motility of the cells. The reprogrammed cells can also remain in the matrix and secrete molecules such as proteins and hormones that will diffuse through the matrix material to the surrounding tissue.

The methods and compositions of the invention may be used to induce the reprogramming of monocytes. This can be used to treat conditions in which there is a loss of specific cells or cell function, such as, for example, in diabetes and Parkinson's disease, although the methods and compositions of the invention can also be used in the treatment of other conditions where specific cells or cell function is desired. Typically the hydrogel will be delivered to the tissue where a cell type or cell function needs to be restored, but can also be delivered to connective tissues, internal organs, and spaces between tissues or organs. Induction of monocyte reprogramming may be achieved by implanting in a tissue a permeable semisolid matrix embedded with liposomes containing expression vectors which encode specific transcription factors. Expression of these transcription factors within the monocyte will induce reprogramming into the desired cell type. Transcription factors that trigger monocyte reprogramming into beta cells include Ngn3, Pdx1 and Mafa. Matrix infiltrating monocytes will phagocyte the liposomes, and the cells then reprogram to become beta cells that produce insulin and are capable of compensating for insulin deficiency in an insulin resistant or insulin deficient subject. Transcription factors that trigger monocyte reprogramming into dopamine secreting cells include one or more of the following: Oct4, Sox2, c-Myc, klf-4, Nanog. Polycomb group (PcG) proteins, PAX6, MEIS1, OTX1, ATBF1, DLX5, HAND1, Nuclear factor kappa-B and OENCUT1.

Additional transcription factors that may be incorporated into liposomes for delivery in accordance with the methods of the invention are described in Qiao Zhou, Juliana Brown, Andrew Kanarek, Jayaraj Rajagopal & Douglas A. Melton. In vivo reprogramming of adult pancreatic exocrine cells to β-cells. Nature 455, 627-632 (2 Oct. 2008), the entire contents of which are incorporated herein by reference.

Additional transcription factors that may be incorporated into liposomes for delivery in accordance with the methods of the invention are likewise described in the following, the entire contents of which are incorporated herein by reference:

Hanna J, Markoulaki S, Schorderet P, Carey B W, Beard C, Wernig M, Creyghton M P, Steine E J, Cassady J P, Foreman R, Lengner C J, Dausman J A, Jaenisch R. (2008) Direct reprogramming of terminally differentiated mature B lymphocytes to pluripotency. Cell. 133(2):250-64.

Wernig M, Zhao J P, Pruszak J, Hedlund E, Fu D, Soldner F, Broccoli V, Constantine-Paton M, Isacson O, Jaenisch R. (2008) Neurons derived from reprogrammed fibroblasts functionally integrate into the fetal brain and improve symptoms of rats with Parkinson's disease. Proc Natl Acad Sci USA. 105(15):5856-61.

Hanna J, Wernig M, Markoulaki S, Sun C W, Meissner A, Cassady J P, Beard C, Brambrink T, Wu L C, Townes T M, Jaenisch R. Treatment of sickle cell anemia mouse model with iPS cells generated from autologous skin. (2007) Science. 318(5858):1920-3.

Wernig M, Meissner A, Foreman R, Brambrink T, Ku M, Hochedlinger K, Bernstein B E, Jaenisch R. In vitro reprogramming of fibroblasts into a pluripotent ES-cell-like state. (2007) Nature. 19; 448(7151):318-24.

Levy Y S, Stroomza M, Melamed E, Offen D. Embryonic and adult stem cells as a source for cell therapy in Parkinson's disease. J Mol Neurosci. 2004; 24(3):353-86

Yamanaka S. Induction of pluripotent stem cells from mouse fibroblasts by four transcription factors. Cell Prolif. 2008 February; 41 Suppl 1:51-6

Erceg S, Laínez S, Ronaghi M, Stojkovic P, Pérez-Aragó M A, Moreno-Manzano V, Moreno-Palanques R, Planells-Cases R, Stojkovic M. Differentiation of human embryonic stem cells to regional specific neural precursors in chemically defined medium conditions. PLoS ONE. 2008 May 7; 3(5):e2122.

The present invention features methods and compositions for endogenous cell therapy which employ an implantable matrix embedded with liposomes. Through phagocytosis, monocytes infiltrating the matrix selectively incorporate the liposomes and their contents. Accordingly, by incorporating liposomes containing specific compounds inside an implantable matrix, it possible to deliver compounds to monocytes and modulate monocyte behavior.

In one aspect, the invention provides an implantable, semisolid matrix comprising a hydrogel material and liposomes embedded therein, wherein the liposomes contain at least one bioactive material, and wherein the matrix is permeable to the infiltration of cells from an implantation environment and to products secreted from the cells into the environment. In one embodiment of this aspect, the bioactive material is selected from the group consisting of a protein, a peptide, a nucleotide, a DNA, a RNA, a siRNA, and a cDNA, or a combination thereof. In another embodiment, the bioactive material is a small molecule, a drug or a combination thereof. In another embodiment, the liposomes contain more than one bioactive material. In an exemplary embodiment, the more than one bioactive materials include a biological and a chemical material.

In another embodiment of this aspect, the liposomes carry the material in the liposomal hydrophilic core, in the membrane on its surface or in a combination thereof. In yet another embodiment, the hydrogel contains a biological or chemical compound that is not carried within the liposomes. In one embodiment, the biological or chemical compound is a chemoattractant protein. In another embodiment, the chemoattractant protein is monocyte chemotactic protein-1.

In one embodiment, the liposomes are attached to the hydrogel matrix by a chemical bond, e.g., a peptide bond or an ionic bond. In another embodiment, the hydrogel material contains cells added to the hydrogel material prior to its implantation in the body. In one embodiment, the cells are monocytes.

In another embodiment, the hydrogel of the matrix comprises copolymers of two or more polyhydroxy acids, polyorthoesters, polyanhydrides, gelatin, collagen, cellulose, derivatized cellulose, chitosan, alginate, hyaluronan, thiol-modified hyaluronan, and combinations or copolymers thereof. In one embodiment, the polyhydroxy acid is polylactic acid, polyglycolic acid or other polyhydroxy acid.

In one embodiment, the matrix further comprises a cross-linking agent. In one embodiment, the cross-linking agent is glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, or tripolyphosphate, or combinations thereof.

In some embodiments, the bioactive material contained within the liposomes is an expression vector encoding a transcription factor. In some embodiments, the transcription factor is capable of differentiating the cell into an insulin producing cell. In exemplary embodiments, the transcription factor is selected from the group consisting of NGN-3, PDX-1, MAFA, Oct4, Sox2, c-Myc, klf-4, Nanog. Polycomb group (PcG) proteins, PAX6, MEIS1, OTX1, ATBF1, DLX5, HAND1, Nuclear factor kappa-B and OENCUT1.

In another aspect, the invention features a method for programming an implantable, semisolid matrix comprising a hydrogel material and liposomes embedded therein to affect the behavior of cell, comprising formulating within the liposomes a compound capable of affecting the cell's behavior, such that the cell infiltrates the semisolid matrix comprising the hydrogel material and takes up the liposomes through phagocytosis or through fusion of the liposome membrane with the cell membrane.

In another aspect, the invention features a method for effecting the behavior of a cell at or near a site of implantation in a subject, comprising implanting at the site an implantable, semisolid matrix comprising a hydrogel material and liposomes embedded therein, wherein the liposomes comprise at least one compound capable of affecting the cell's behavior, such that the cell infiltrates the semisolid matrix comprising the hydrogel material and takes up the liposomes through phagocytosis or through fusion of the liposome membrane with the cell membrane.

In one embodiment of the foregoing aspects, the behavior is differentiation and/or reprogramming. In an exemplary embodiment, the behavior is differentiation into insulin producing cells. In another exemplary embodiment, the behavior is differentiation into dopamine producing cells. In various embodiments, the cell is, for example, a monocyte, a stem cell, or a stem cell precursor. In exemplary embodiments, the site of implantation of the matrix is within the pancreas or within the brain.

In other embodiments of the foregoing aspects, the compound capable of affecting the cell's behavior is an expression vector. In an exemplary embodiment, the expression vector encodes a transcription factor capable of differentiating the cell into an insulin producing cell. In exemplary embodiments, the transcription factor is, for example, NGN-3, PDX-1, MAFA, Oct4, Sox2, c-Myc, klf-4, Nanog. Polycomb group (PcG) proteins, PAX6, MEIS1, OTX1, ATBF1, DLX5, HAND1, Nuclear factor kappa-B, OENCUT1, or a combination thereof.

In another aspect, the invention features a method for promoting insulin secretion at a localized site in a subject comprising, providing at the localized site an implantable, semisolid matrix comprising a hydrogel material and liposomes embedded therein, wherein the liposomes comprise an expression vector encoding a transcription factor capable of differentiating a cell into an insulin producing cell, and maintaining the matrix or composition at the localized site for a period of time sufficient for a cell to infiltrate the matrix and phagocytose the liposomes, such that the transcription factor is expressed in the cell, thereby promoting differentiation of the cell to produce insulin at the localized site. In an exemplary embodiment, the subject is an insulin resistant subject or an insulin deficient subject.

VIII. Articles of Manufacture

The present invention provides kits that comprise a hydrogel material, reagents for making liposomes, and instructions for the use of the hydrogel material to form a semi-solid matrix comprising liposomes embedded within. In some embodiments, the kit includes liposome reagents including, but not limited to, a phospholipid e.g., distearoyl-phosphatidylglycerol (DSPG), 1,2-distearoyl-sn-glycero-3-phosphocholine (DSPC), dioleoyl phosphatidyl choline (PC), phosphatidic acid (PA), and/or phosphatidylglycerol (PG). In other embodiments, the kit includes one or more of the saturated lipids Dimyristoylphosphatidylcholine (DMPC), dipalmitoyl phosphatidylcholine (DPPC), dipalmitoyl phosphatidic acid (DPPA), and dipalmitoyl phosphatidylglycerol (DMPG). In exemplary embodiments, stearylamine is used when cationic liposomes are preferred. and natural acidic lipids, such as phosphatidylserine (PS), PG, phosphatidylinositol (PI), PA, and cardiolipin (CL) are added when anionic liposomes are desired. In exemplary embodiments, cholesterol can be included to stabilize the bilayer. In exemplary embodiments, small amounts of anti-oxidants, including but not limited to α-tocopherol or β-hydroxytoluidine (BHT), can be included when polyunsaturated neutral lipids are used.

In some embodiments, the kit includes instructions for producing liposomes. In other embodiments, the instructions describe particular biological or chemical compounds that may be incorporated into the liposomes. The instructions can additionally describe particular biological or chemical compounds that are preferably selected for incorporation into the liposomes to modulate a particular behavior of phagocytic cells, e.g., monocytes. In some embodiments, a kit comprises a cross-linking agent for cross-linking the hydrogel to form a semi-solid matrix. In some embodiments, a kit includes instructions for combining the hydrogel material, liposomes and, in particular embodiments, a cross-linking agents, such that an injectable liquid is formed that transitions to a semi-solid matrix following injection into a subject. In some embodiments, instructions are provided in a kit of the invention for including one or more agents capable of recruiting cells, e.g., monocytic cells, to the matrix.

Aspects of the invention include kits that comprise one or more hydrogels, and may comprise polylactic acid, polyglycolic acid, other polyhydroxy acids, copolymers of two or more polyhydroxy acids, polyorthoesters, polyanhydrides, gelatin, collagen, cellulose, derivatized cellulose, chitosan, alginate, thiol-modified hyaluronan, and/or combinations thereof. In some embodiments, a cross-linking agent is comprised by a kit of the invention and may comprise glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, and tripolyphosphate.

Further embodiments of the invention include a kit comprising a hydrogel material, reagents for making liposomes, and instructions for the use of the hydrogel material to form a semi-solid matrix comprising liposomes embedded within. In some embodiments, the kit includes liposome reagents including, but not limited to, a phospholipid e.g., distearoyl-phosphatidylglycerol (DSPG), 1,2-distearoyl-sn-glycero-3-phosphocholine (DSPC), dioleoyl phosphatidyl choline (PC), phosphatidic acid (PA), and/or phosphatidylglycerol (PG). In other embodiments, the kit includes one or more of the saturated lipids Dimyristoylphosphatidylcholine (DMPC), dipalmitoyl phosphatidylcholine (DPPC), dipalmitoyl phosphatidic acid (DPPA), and dipalmitoyl phosphatidylglycerol (DMPG). In exemplary embodiments, stearylamine is used when cationic liposomes are preferred. and natural acidic lipids, such as phosphatidylserine (PS), PG, phosphatidylinositol (PI), PA, and cardiolipin (CL) are added when anionic liposomes are desired. In exemplary embodiments, cholesterol can be included to stabilize the bilayer. In exemplary embodiments, small amounts of anti-oxidants, including but not limited to α-tocopherol or β-hydroxytoluidine (BHT), can be included when polyunsaturated neutral lipids are used.

In some embodiments, the kit may additionally include a buffer suitable for use in preparing liposomes (e.g., 0.9% NaCl). In some embodiments, a kit comprises a cross-linking agent for cross-linking the hydrogel to form a semi-solid matrix. In some embodiments, a kit includes instructions for combining the hydrogel material, liposomes and, in particular embodiments, one or more cross-linking agents, such that an injectable liquid is formed that transitions to a semi-solid matrix following injection into a subject. In some embodiments, instructions are provided in a kit of the invention for including one or more agents capable of recruiting cells, e.g., monocytic cells, to the matrix.

Additional aspects of the invention include kits that comprise one or more hydrogels, and may comprise polylactic acid, polyglycolic acid, other polyhydroxy acids, copolymers of two or more polyhydroxy acids, polyorthoesters, polyanhydrides, gelatin, collagen, cellulose, derivatized cellulose, chitosan, alginate, thiol-modified hyaluronan, and/or combinations thereof. In some embodiments, a cross-linking agent provided with a kit of the invention may comprise glutaraldehyde, diphenylphosphoryl azide, transglutaminase, dimethyl suberimidate, DMS-treated collagen, dimethyl 3,3'-dithiobispropionimidate, multivalent ions, calcium ions, N,N methylene-bisacrylamide (MBA), acrylamide, allyl methacrylate, ethylene glycol dimethacrylate, and tripolyphosphate.

In particular embodiments, the kits, or articles of the invention further comprise one or more bioactive molecules or chemical compounds for incorporation into the liposome matrix.

IX. Polycaprolactone Particles as Scaffolds for Tissue Regeneration

Tissue engineering involves a combination of cells, engineering and materials methods, and suitable biochemical and physio-chemical factors to improve or replace biological functions. In practice, tissue engineering is closely associated with applications that repair or replace portions of or whole tissues (i.e., bone, cartilage, blood vessels, bladder, etc.). Often, the tissues involved require certain mechanical and structural properties for proper functioning.

Scaffolds are artificial structures capable of supporting three-dimensional tissue formation. Scaffolds usually serve at least one of the following purposes: allowing cell attachment and migration; delivering and retaining cells and biochemical factors; enabling diffusion of vital cell nutrients and expressed products; or exertion of certain mechanical and biological influences to modify the behavior of the cell phase.

To achieve the goal of tissue reconstruction, scaffolds must meet some specific requirements. A high porosity and an adequate pore size are necessary to facilitate cell seeding and diffusion throughout the whole structure of both cells and nutrients. Biodegradability is often an essential factor since scaffolds should preferably be absorbed by the surrounding tissues without the necessity of a surgical removal.

In one embodiment, the present invention relates to methods of using polycaprolactone (PCL) particles as biodegradable scaffolds in tissue engineering applications.

In one embodiment, the application is directed to methods of promoting tissue regeneration, the method comprising contacting a localized area of tissue with solvent-free polycaprolactone (PCL) particles.

In another embodiment, the application is directed to a dermal filler comprising a solvent-free polycaprolactone (PCL) scaffold for the attachment of skin fibroblasts.

In another embodiment, the application is directed to an angiogenic hydrogel comprising a solvent-free polycaprolactone (PCL) scaffold and one or more of copolymers of two or more polyhydroxy acids, polyorthoesters, polyanhydrides, gelatin, collagen, cellulose, derivatized cellulose, chitosan, alginate, hyaluronan, thiol-modified hyaluronan, and combinations or copolymers thereof.

In the present invention, PCL is used to generate the micro-particles. PCL is a biocompatible and biodegradable polymer. In the present invention, the micro particles are generated with PCL by means of physical methods such as grinding, milling, chopping and/or molding the polymer base material, and without using organic solvents.

The PCL particles can then be assembled in a way that will serve as a scaffold. In one of the embodiments, the PCL particles have a rod shape, and are aggregated in a hay bed manner.

In another embodiment the PCL particles are embedded within a hydrogel matrix such as collagen or hyaluronic acid that help hold the particles in place following their delivery in the body.

In another embodiment the PCL particles serve as a bed for the attachment of fibroblasts In one embodiment, the invention is related to a method of promoting tissue regeneration, the method comprising contacting a localized area of tissue with solvent-free polycaprolactone (PCL) particles. In an exemplary embodiment the PCL particle size ranges from 1-1000 microns, for example 5-50 microns.

In another embodiment the PCL particles are processed by grinding, milling, chopping and/or molding.

In one embodiment the PCL particles are embedded within a hydrogel. The hydrogel comprises one or more copolymers comprising two or more polymers selected from polyhydroxy acids, polyorthoesters, polyanhydrides, gela-

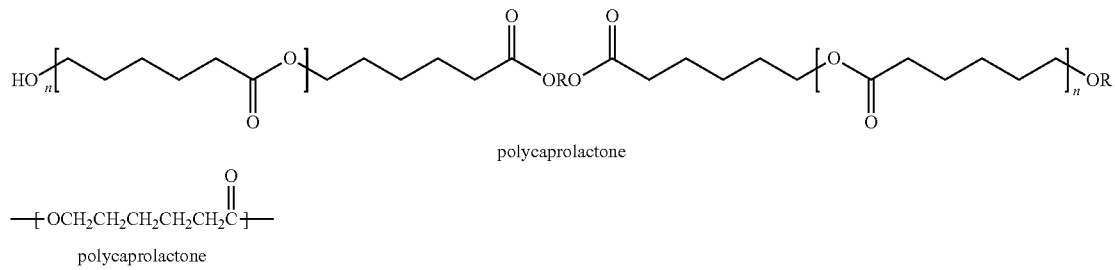

polycaprolactone polycaprolactone

Methods for the production of PCL particles are described by Iooss and Kuang. (P. Iooss. Biomaterials. Volume 22, Issue 20, 15 Oct. 2001, Pages 2785-2794; M. Lebourg. J Mater Sci: Mater Med (2008) 19:2047-2053; Lim Liang Kuang. Journal of Controlled Release. Volume 102, Issue 2, 2 Feb. 2005, Pages 395-413.)

The methods described in the art for the production of PCL particles include the use of an organic solvent, which makes it unpractical for clinical use in tissue regeneration applications. After using organic solvent in the production, some traces of it may remain in the final product, which may have a potentially hazardous effect on the safety of the polymer in vivo, when the polymer is expected to stay in vivo for a long time (more than one month). Currently, PCL particles created with organic solvents are used for controlled drug delivery, where the particle will stay in vivo for only a few days, or for coating medical devices in conjunction with other materials in which immunosuppressants are given to prevent an immune response.

In the present invention, the production of PCL particles is performed by physical processes and without the use of organic solvents. PCL particles are generated by means of physical processes such as grinding, milling chopping and/ or molding the polymer base material, as described, for example, in WO/1993/006267 which is hereby incorporated by reference for the purpose of teaching such processes. After processing PCL into particles the particles can be filtered to restricted size in order to obtain maximum particle size. The minimal size of a particle will be determined by the thickness of the filament used.

tin, collagen, cellulose, derivatized cellulose, chitosan, alginate, hyaluronan, thiol-modified hyaluronan, and combinations or copolymers thereof.

In one embodiment, the tissue is contacted by surgical implantation. In another embodiment, the tissue is contacted by injection. In yet another embodiment, the tissue is contacted by topical application.

In an exemplary embodiment, the localized area of tissue is selected from physically wounded, necrotic, ischemic or dermal tissue. In a preferred embodiment, the localized area of tissue is dermal tissue.

In one embodiment of the invention, the polycaprolactone (PCL) particles are used in the production of scaffolds for dermal fillers in cosmetic interventions. In this embodiment, the particles should comply with the following requirements:

(1) Biocompatibility, not inducing an immune response and generating only minimal inflammation;
(2) Have good shape memory in order to maintain shape while the product is injected under the skin;
(3) Have good shape memory so that injected locations will retain shape for a long period of time (1-24 months, preferably 12-18 months) under the skin, where mechanical forces are routinely inflicted on the skin. The scaffold material should be sufficiently stable to last for a predictable period of time without losing its dual therapeutic effects a) as filler and b) as a scaffold for attachment of skin fibroblasts;
(4) The scaffold within the dermal filler should act as a bed for the attachment and propagation of skin fibroblasts. Fibroblasts attached to the scaffold material will proliferate, secrete collagen and regenerate the connective tissue in the wrinkle area; and/or (5) The scaffold should degrade slowly over a long period of time, without disrupting the cells embedded in the scaffold. By the time in which the scaffold is completely absorbed (1-24 months, preferably 12-18 months), the connective tissue produced will remain and therefore will fill the space of the scaffold after the scaffold has been absorbed.

In an exemplary embodiment, the dermal filler comprises a solvent-free polycaprolactone (PCL) scaffold for the attachment of skin fibroblasts.

In another exemplary embodiment, the dermal fillers are an injectable material used in contouring and volumising facial wrinkles and folds. They can also be used to create definition and pouting of the lips.

Dermal fillers are a class of biodegradable scaffolds used to help reverse the changes associated with aging. As skin ages, the dermis gradually loses its major constituents: collagen, elastin and hyaluronic acid. Collagen acts as the major support protein for our skin; elastin allows our skin to stay firm and resist wrinkles; hyaluronic acid helps to trap water and add volume and shape to our skin. Because the goal is to return the dermis to its original youthful state, dermal fillers can give a more natural appearance than surgical face lifts. Dermal fillers are being used to reduce or eliminate wrinkles, raise scar depressions, enhance lips, and replace soft-tissue volume loss.

In other embodiment of the invention, the PCL particles are used in the production of scaffolds for angiogenic gel-based therapies. The angiogenic gel-based therapy can be used in the treatment of limb ischemia, wound healing, tissue grafting, ischemic heart disease, ischemic brain, etc. In this embodiment, the particles should comply with the following requirements:

(1) Biocompatibility, not inducing an immune response and generating only minimal inflammation;

(2) Have good shape memory in order to maintain shape while the product is injected into the muscle tissue and/or subcutaneous tissue;

(3) Have good shape memory in order to maintain shape for a long period of time (1-24 months, preferably 12-18 months or 3-6 months) in muscle tissue or connective tissue, where mechanical forces are routinely inflicted. The scaffold material should be sufficiently stable to last for a predictable period of time without losing its therapeutic effect as a mechanical scaffold for the generation of 3 dimensional spherical constructs in the place of injection; and/or (4) The PCL-based scaffold should act as a bed for the attachment of leucocytes and in particular monocytes. Leucocytes attached to the scaffold material or embedded next to the scaffold will have an ischemic microenvironment. For example, monocytes in an ischemic environment will switch into their angiogenic phenotype and will secrete a cascade of vascular growth factors such as vascular endothelial growth factor into the surrounding tissue, promoting the growth of new blood vessels.

In one embodiment, the angiogenic hydrogel comprises a solvent-free polycaprolactone (PCL) scaffold and a hydrogel comprising one or more copolymers comprising two or more polymers selected from polyhydroxy acids, polyorthoesters, polyanhydrides, gelatin, collagen, cellulose, derivatized cellulose, chitosan, alginate, hyaluronan, thiol-modified hyaluronan, and combinations or copolymers thereof.

In another embodiment, the angiogenic hydrogel is used to treat ischemia, for example, limb ischemia, ischemic heart disease or ischemic brain. In one embodiment, the angiogenic hydrogel is used to treat wounds. In yet another embodiment, the angiogenic hydrogel is used for tissue grafting.

In an exemplary embodiment, the angiogenic gel-based therapy is a hydrogel composition that promotes the growth of new blood vessels by changing the phenotype of cells that infiltrate the hydrogel so they will secret angiogenic growth factors.

The foregoing disclosure teaches to those of skill in the art the aspects of the invention including how to make and use the invention. The following examples are meant to provide further elucidation of the invention and are not meant to be limiting.

EXAMPLES

Example 1: Localized Differentiation of Endogenous Monocytes into an Angiogenic Phenotype a. Preparation of Liposomes Containing IL-4 and IL-10 and Liposomes Containing Adenosine.
Reagents
Dioleoyl Phosphatidyl Choline
Saline (0.9% NaCl)

Human recombinant IL-4 and IL-10 are used together to activate the angiogenic phenotype in monocytes.

Adenosine can be used alone or in combination with IL-4 and IL-10 to activate the angiogenic phenotype in monocytes.

Method of Producing Liposomes Containing IL-4 and IL-10 for Targeting of Monocytes
Under aseptic conditions:
1. Dry 0.5 µmole of dioleoyl phosphatidyl choline under nitrogen in a disposable glass tube.
2. Evacuate in dessicator under vacuum for 30 minutes.
3. Add saline to required volume and scrape the sides of the glass tube to dislodge the lipid.
4. Add IL-4 and IL-10 1 µg/µl of lipid used, and, optionally adenosine 200 µM.
5. Vortex for 30 seconds. Sonicate twice in a bath sonicator at 7° C. for 1 min. This makes multilamellar vesicles that become small unilamellar vesicles (SUV) with prolonged sonication time. To make large unilamellar vesicles, use an extruder.

Method of Producing Liposomes Containing Adenosine for Targeting of Monocytes

Adenosine is encapsulated in liposomes composed of 50 µmol/L distearoyl-phosphatidylglycerol (DSPG), 100 µmol/L cholesterol, and 150 µmol/L of 1,2-distearoyl-sn-glycero-3-phosphocholine (DSPC) by reverse-phase evaporation technique, as described by Mönkkönen J, Taskinen M, Auriolal S O K, et al. J Drug Target. 1994; 2: 299-308. Liposomes with average size of 150 nm are produced composed of 0.5 mmol/L, and 20 mmol/L, adenosine and lipids, respectively.

b. Preparation of the Semisolid Hydrogel Matrix with Liposomes for Delivery of Liposomes Containing IL-4 and IL-10

Type 1 collagen solution 4 mg/ml in saline in neutral pH is freshly prepared and kept on ice to delay gelation. $2\times10^6$ liposomes in 200 µl saline are added to 200 µL of the liquid collagen and mixed gently. Gelatin powder (e.g., Gelfoam powder) can be added to the collagen solution in order to increase and maintain volume in the injection site and to increase monocyte attraction. The use of specific monocyte chemoattractants such as monocyte chemotactic protein-1 (MCP1) within the matrix can also be used to attract monocytes to the matrix. For this purpose, MCP1, 1 µg/ml can be incorporated within the matrix.

c. Localized Delivery of the Hydrogel Embedded with Liposomes

The collagen solution with the suspended liposomes is injected to the patient where needed. For example if the differentiation is towards an angiogenic phenotype, the delivery will be to an ischemic muscle tissue. The patient's monocytes will invade the matrix and phagocyte the liposomes resulting in uptake of the delivered cytokines or adenosine and activation/differentiation of the monocytes/macrophages.

Example 2: Presentation of Cancer Cell Antigens to Monocytes/Dendritic Cells in the Vicinity of a Tumor a. Preparation of Patient Specific Tumor Antigens Tumor cells are taken by biopsy from a patient. The cells are lysed mechanically or by using a surface active material such as triton-X100. If surface antigens from the patient's cancer cells are required, cells can be incubated in a hypotonic buffer such as distilled water to remove cell content, and protein can then be extracted from the membranes. Protein extract from the cells is filtered to remove surface active materials and resuspended in saline solution. The protein extract from the cells is used for loading into liposomes. Proteins are loaded inside the liposomes to be phagocytosed by monocytes infiltrating the implanted matrix.

b. Preparation of the Liposomes Containing Tumor Antigens
Reagents
Dioleoyl Phosphatidyl Choline
Saline (0.9% NaCl)
Method
Under aseptic conditions:
1. Dry 0.5 µmole of dioleoyl phosphatidyl choline under nitrogen in a disposable glass tube.
2. Evacuate in dessicator under vacuum for 30 minutes.
3. Add Saline to required volume and scrape the sides of the glass tube to dislodge the lipid.
4. Add protein extracted from cancer cells at 1 µg/µl of lipid used and macrophage colony-stimulating factor at 1 µg/µl of lipid used.
5. Vortex for 30 seconds. Sonicate twice in a bath sonicator at 7° C. for 30 sec. This makes multilamellar vesicles that become small unilamellar vesicles (SUV) with prolonged sonication time. To make large unilamellar vesicles, an extruder can be used.

Alternative Method to Produce Liposomes Containing Cancer Antigens for Targeting of Monocytes:

Protein is extracted from cancer cells as described above. Protein at 1 µg/µl of lipid used, and macrophage colony-stimulating factor (GM-CSF) at 1 µg/µl of lipid used, is encapsulated in liposomes composed of 50 µmol/L distearoyl-phosphatidylglycerol (DSPG), 100 pmol/L cholesterol, and 150 µmol/L of 1,2-distearoyl-sn-glycero-3-phosphocholine (DSPC) by reverse-phase evaporation technique, as described by Mönkkönen J, Taskinen M, Auriolal S O K, et al. J Drug Target. 1994; 2: 299-308. Liposomes with average size of 150 nm are produced containing the cancer antigens and (GM-CSF).

c. Preparation of the Semisolid Hydrogel Matrix for Delivery of Liposomes Containing Tumor Antigens Type 1 collagen solution at 4 mg/ml in saline at neutral pH is freshly prepared and kept on ice to delay gelation. $10^7$ liposomes in 200 µl saline are added to 200 µL of the liquid collagen and mixed gently. The collagen solution with the suspended liposomes is injected to the same patient in the vicinity of the tumor from which the biopsy was taken and protein extracted.

d. Localized Delivery of the Hydrogel Embedded with Liposomes Containing Tumor Antigens The collagen solution with the suspended liposomes is injected to the patient in the vicinity of the tumor. The patient's monocytes will invade the matrix and phagocytose the liposomes resulting in uptake of the tumor antigens and activation/differentiation to dendritic cells. The dendritic cells will then ether exit the matrix as it degrades and will interact with T-cells in their surrounding environment, or will interact with infiltrating T-cells in the matrix. The activated T-cells will initiate a cell-mediated immune response aimed towards the tumor cells.

Example 3: Localized Reprogramming of Endogenous Monocytes or Stem Cells into Functional Insulin-Producing Beta Cells in the Pancreas a. Preparation of Liposomes Containing Expression Vectors that Encode Transcription Factors
Reagents
Dioleoyl Phosphatidyl Choline
Saline (0.9% NaCl)
Method
Under aseptic conditions:
1. Dry 0.5 µmole of dioleoyl phosphatidyl choline under nitrogen in a disposable glass tube.
2. Evacuate in dessicator under vacuum for 30 minutes.
3. Add saline to required volume and scrape the sides of the glass tube to dislodge the lipid.
4. Add expression vectors that encode Ngn3, Pdx1 and Mafa, 0.1 µg/µl of lipid used.
5. Vortex for 30 seconds. Sonicate twice in a bath sonicator at 7° C. for 30 sec. This makes multilamellar vesicles that become small unilamellar vesicles (SUV) with prolonged sonication time. To make large unilamellar vesicles, an extruder can be used.

Another Method to Produce Liposomes Containing Transcription Factors for Targeting Monocytes:

Expression vectors encoding Ngn3, Pdx1 and Mafa (0.1 µg/µl of lipid used) are encapsulated in liposomes composed of 50 µmol/L distearoyl-phosphatidylglycerol (DSPG), 100 µmol/L cholesterol, and 150 µmol/L of 1,2-distearoyl-sn-glycero-3-phosphocholine (DSPC) by reverse-phase evaporation technique. Reverse-phase evaporation technique is described by Mönkkönen J, Taskinen M, Auriolal S O K, et al. J Drug Target. 1994; 2: 299-308, incorporated herein by reference in its entirety. Liposomes with average size of 150 nm are produced.

b. Preparation of the Semisolid Hydrogel Matrix for Delivery of Liposomes Containing Transcription Factors Type 1 collagen solution (4 mg/ml in saline at neutral pH) is freshly prepared and kept on ice to delay gelation. $2 \times 10^6$ liposomes in 200 µl saline are added to 200 µL of the liquid collagen and mixed gently. Gelatin powder (Gelfoam powder can be added to the collagen solution in order to increase and maintain volume in the injection site and to increase monocyte attraction. The use of specific monocyte chemoattractants such as monocyte chemotactic protein-1 within the matrix can also be used to attract monocytes to the matrix. Alternatively the liposomes can be added to the semisolid collagen gel and mixed with the semisolid gel to produce a mixture of gel particles and liposomes.

c. Localized Delivery of the Hydrogel Embedded with Liposomes Containing Transcription Factors into the Pancreas The collagen solution with the suspended liposomes is injected to the pancreas. The patient's monocytes will invade the matrix and phagocyte the liposomes resulting in uptake of the delivered transcription factors and the reprogramming/differentiation into functional insulin-producing beta cells.

Although the foregoing invention has been described in detail for purposes of clarity of understanding, it will be obvious that certain modifications may be practiced within the scope of the appended claims. All publications and patent documents cited herein, as well as text appearing in the figures, are hereby incorporated by reference in their entirety for all purposes to the same extent as if each were so individually denoted.

What is claimed is:

1. A method of inducing an angiogenic phenotype in endogenous monocytes to thereby secrete vascular growth factors at a localized site in a subject, the method comprising:
injecting a semisolid matrix comprising a hydrogel and liposomes embedded therein, at an implantation site in a subject, wherein said liposomes have a size in the range of 25 to 400 nm and contain one or more bioactive materials which differentiate endogenous monocytes into cells that have an angiogenic phenotype and secrete at least one vascular growth factor, wherein the bioactive material is selected from the group consisting of a small molecule, a peptide, or a protein;
allowing the hydrogel to polymerize around the liposomes at the implantation site; and
maintaining the hydrogel in the subject for a period of time sufficient for endogenous monocytes to infiltrate the hydrogel and phagocytose the liposomes, thereby releasing the bioactive material from the liposomes into the endogenous monocytes;
wherein release of the bioactive material from the liposomes to the infiltrating endogenous monocytes upon phagocytosis causes the infiltrating endogenous monocytes to adopt an angiogenic phenotype characterized by secretion of vascular growth factors, such that at least one vascular growth factor is secreted by the endogenous monocytes in the environment of the hydrogel.

2. The method of claim 1, wherein the bioactive material is selected from the group consisting of a toll-like receptor 2 (TLR2) agonist, a toll-like receptor 3 (TLR3) agonist, a toll-like receptor 4 (TLR4) agonist, a toll-like receptor 7 (TLR7) agonist, a toll-like receptor 8 (TLR8) agonist, a toll-like receptor 9 (TLR9) agonist, an adenosine A1 agonist, an adenosine A2 agonist, an adenosine A3 agonist, and combinations thereof.

3. The method of claim 1, wherein the endogenous monocytes having an angiogenic phenotype secrete vascular endothelial growth factor (VEGF).

4. The method of claim 3, wherein the endogenous monocytes having an angiogenic phenotype further secrete a therapeutic protein selected from the group consisting of fibroblast growth factor (FGF), platelet derived growth factor (PDGF), hepatocyte growth factor/scatter factor (HGF/SF), epidermal growth factor (EGF), interleukin-8 (IL-8), and combinations thereof.

5. The method of claim 1, wherein the endogenous monocytes having an angiogenic phenotype further secrete an immunosuppressive factor.

6. The method of claim 5, wherein the immunosuppressive factor is selected from the group consisting of interleukin 4 (IL-4), interleukin 10 (IL-10), transforming growth factor-β (TGF-β), and combinations thereof.

7. The method of claim 1, wherein the hydrogel comprises one or more polymers selected from the group consisting of polylactic acid, polyglycolic acid, polyhydroxy acid, copolymers of two or more polyhydroxy acids, polyorthoesters, polyanhydrides, gelatin, collagen, cellulose, derivatized cellulose, chitosan, alginate, hyaluronan, thiol-modified hyaluronan, and combinations or copolymers thereof.

8. The method of claim 1, wherein the hydrogel comprises collagen.

9. The method of claim 1, wherein the hydrogel comprises hyaluronic acid.

10. The method of claim 1, wherein the hydrogel comprises a cross-linking agent.

11. The method of claim 10, wherein the cross-linking agent is selected from the group consisting of glutaraldehyde, diphenylphosphoryl azide, transglutaminase, dimethyl suberimidate, DMS-treated collagen, dimethyl 3,3'dithiobispropionimidate, multivalent ions, calcium ions, N,N methylene-bisacrylamide (MBA), acrylamide, allyl methacrylate, ethylene glycol dimethacrylate, tripolyphosphate, and combinations thereof.

12. The method of claim 1, wherein the hydrogel comprises a chemoattractant.

13. The method of claim 12, wherein the chemoattractant is monocyte chemotactic protein-1 (MCP-1).

14. The method of claim 1, wherein the bioactive material is selected from the group consisting of adenosine, interleukin-4 (IL-4), interleukin-10 (IL-10), and combinations thereof.

15. The method of claim 1, wherein the bioactive material is selected from the group consisting of interleukin-10 (IL-10), interleukin-4 (IL-4), interleukin-13 (IL-13), an interleukin-1 (IL-1) receptor ligand, prostaglandin E2 (PGE2), transforming growth factor β (TGF-β), tumor necrosis factor α (TNFα), lactic acid, lipoteichoic acid, nicotinamide adenine dinucleotide hydrate (NADH) dehydrogenase 5, subunit 1, poly (adenosine diphosphate-ribose) polymerase, pyruvate, Colony Stimulating Factor-1, an adenosine analogue, 5'-N-[adenine-2,8-3H]-ethylcarboxamidoadenosine (NECA), lipopolysaccharide (LPS), Pam3CSK4, E. coli lipopolysaccharide (LPS), R848, imiquimod, non-methylated CpG DNA, ODN2006, thioredoxin peroxidase, Trapidil, Alendronate, and combinations thereof.

16. The method of claim 1, wherein the subject has or is at risk for a condition selected from the group consisting of coronary artery disease, peripheral artery disease, limb ischemia, ischemic wound, ischemic ulcer, ischemic bowel disease, atherosclerotic ischemic disease, muscle flaps, skin flaps, organ transplant, nasolabial folds, and wrinkles.

17. The method of claim 1, wherein the implantation site is a site of ischemia.

18. The method of claim 1, wherein the bioactive material is adenosine.

19. The method of claim 1, wherein the liposomes are selected to be between 100 and 200 nm.

20. A method of reprogramming endogenous monocytes to secrete a vascular growth factor to a localized site of ischemia in a subject, comprising:

injecting a matrix comprising a hydrogel and liposomes embedded therein, at an ischemic site in a subject, wherein the liposomes have a size in a range of 25 nm to 400 nm and contain adenosine or an adenosine analog in an amount sufficient to differentiate endogenous monocytes into cells that secrete a vascular growth factor;

allowing the hydrogel to polymerize around the liposomes at the implantation site; and maintaining the hydrogel in the subject for a period of time sufficient for endogenous monocytes to infiltrate the hydrogel and phagocytose the liposomes, thereby releasing the adenosine or adenosine analog from the liposomes into the endogenous monocytes;

wherein release of the adenosine or adenosine analog from the liposomes to the infiltrating endogenous monocytes upon phagocytosis causes differentiation of the endogenous monocytes into cells that secrete a vascular growth factor, such that the vascular growth factor is secreted by the endogenous monocytes in the environment of the hydrogel.

21. The method of claim 20, wherein the liposomes are selected to be between 100 and 200 nm.

22. The method of claim 20, wherein the vascular growth factor is vascular endothelial growth factor (VEGF).

23. The method of claim 20, wherein the hydrogel comprises a chemoattractant.

24. The method of claim 23, wherein the chemoattractant is monocyte chemotactic protein-1 (MCP-1).

\* \* \* \* \*